(12) United States Patent
Sako

(10) Patent No.: US 6,671,394 B1
(45) Date of Patent: Dec. 30, 2003

(54) IMAGE PROCESSING APPARATUS, IMAGE PROCESSING METHOD, AND RECORDING MEDIA

(75) Inventor: Tsukasa Sako, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/385,056

(22) Filed: Aug. 30, 1999

(30) Foreign Application Priority Data

Aug. 31, 1998 (JP) ............................................. 10-260900

(51) Int. Cl.[7] .................................................. G06K 9/00
(52) U.S. Cl. ................................... 382/132; 250/370.09
(58) Field of Search ................................. 382/128, 132, 382/133, 274, 100, 141, 181, 219, 298; 250/370.09, 586, 584; 378/28, 4, 62, 98.2, 98.8; 600/300

(56) References Cited

U.S. PATENT DOCUMENTS

| | | | | | |
|---|---|---|---|---|---|
| 4,323,779 A | * | 4/1982 | Albert | ....................... | 378/98.6 |
| 4,933,961 A | * | 6/1990 | Rushbrooke et al. | ......... | 378/57 |
| 4,975,935 A | * | 12/1990 | Hillen et al. | .................. | 378/28 |
| 5,151,947 A | * | 9/1992 | Nagatsuka et al. | ......... | 382/132 |
| 5,241,471 A | * | 8/1993 | Trousset et al. | ............ | 382/274 |
| 5,268,967 A | * | 12/1993 | Jang et al. | .................. | 382/132 |
| 5,604,781 A | * | 2/1997 | Suzuki et al. | .................. | 378/62 |
| 5,615,279 A | * | 3/1997 | Yoshioka et al. | ........... | 382/131 |
| 5,664,001 A | * | 9/1997 | Tachibana et al. | ......... | 378/98.8 |
| 5,668,889 A | * | 9/1997 | Hara | ........................... | 382/132 |
| 5,828,775 A | * | 10/1998 | Takeo et al. | ................. | 382/132 |
| 6,084,939 A | * | 7/2000 | Tamura | ....................... | 378/98.2 |
| 6,314,198 B1 | | 11/2001 | Ogura | ......................... | 382/132 |
| 2002/0114504 A1 | | 8/2002 | Shinbata | ..................... | 382/132 |

OTHER PUBLICATIONS

U.S. application Ser. No. 09/385,048, filed Aug. 30, 1999.
U.S. application Ser. No. 09/408,447, filed Sep. 29, 1999.

* cited by examiner

*Primary Examiner*—Jayanti K. Patel

(57) ABSTRACT

An image processing apparatus capable of speedy processing and cost reduction is provided. A generating apparatus reduces an original image as a display image or the like, and generates a reduced image. An image processing apparatus performs image processing for the generated reduced image by the generating apparatus based on a set first image processing condition. An image correction apparatus performs image correction for the original image based on a set second image processing condition. At this time, the first and second image processing conditions are associated with each other according to the reduction conditions for the generating apparatus.

16 Claims, 26 Drawing Sheets

FIG. 18

| PROCESSING CONTENT | SETTING METHOD | DEFAULT VALUE | PARAMETER FOR NATURAL REDUCTION IMAGE PROCESS | PARAMETER FOR NATURAL IMAGE PROCESS |
|---|---|---|---|---|
| (1) IRRADIATION FIELD RECOGNITION | AUTOMATIC | AUTOMATIC | AUTOMATIC | 8 TIMES DETERMINED VALUE |
| | DESIGNATE | X, Y, W, H | COORDINATE SYSTEM X/8, Y/8, W/8, H/8 OF 1/8 TIMES DEFAULT VALUE | COORDINATE SYSTEM OF 8 TIMES DETERMINED VALUE |
| (2) IMAGE EMPHASIS | 0 (NORMAL) 10 (THIN) 20 (MIDDLE) 30 (STRONG) | N | 1/2 TIMES DEFAULT N | 2 TIMES DETERMINED VALUE |
| (3) GRADATION CONVERSION | AUTOMATIC | AUTOMATIC | AUTOMATIC | EQUAL TO DETERMINED VALUE |

ATTENTION : NATURAL IMAGE IS 2688×2688×12 BITS, NATURAL REDUCTION IMAGE IS 336×336×12 BITS

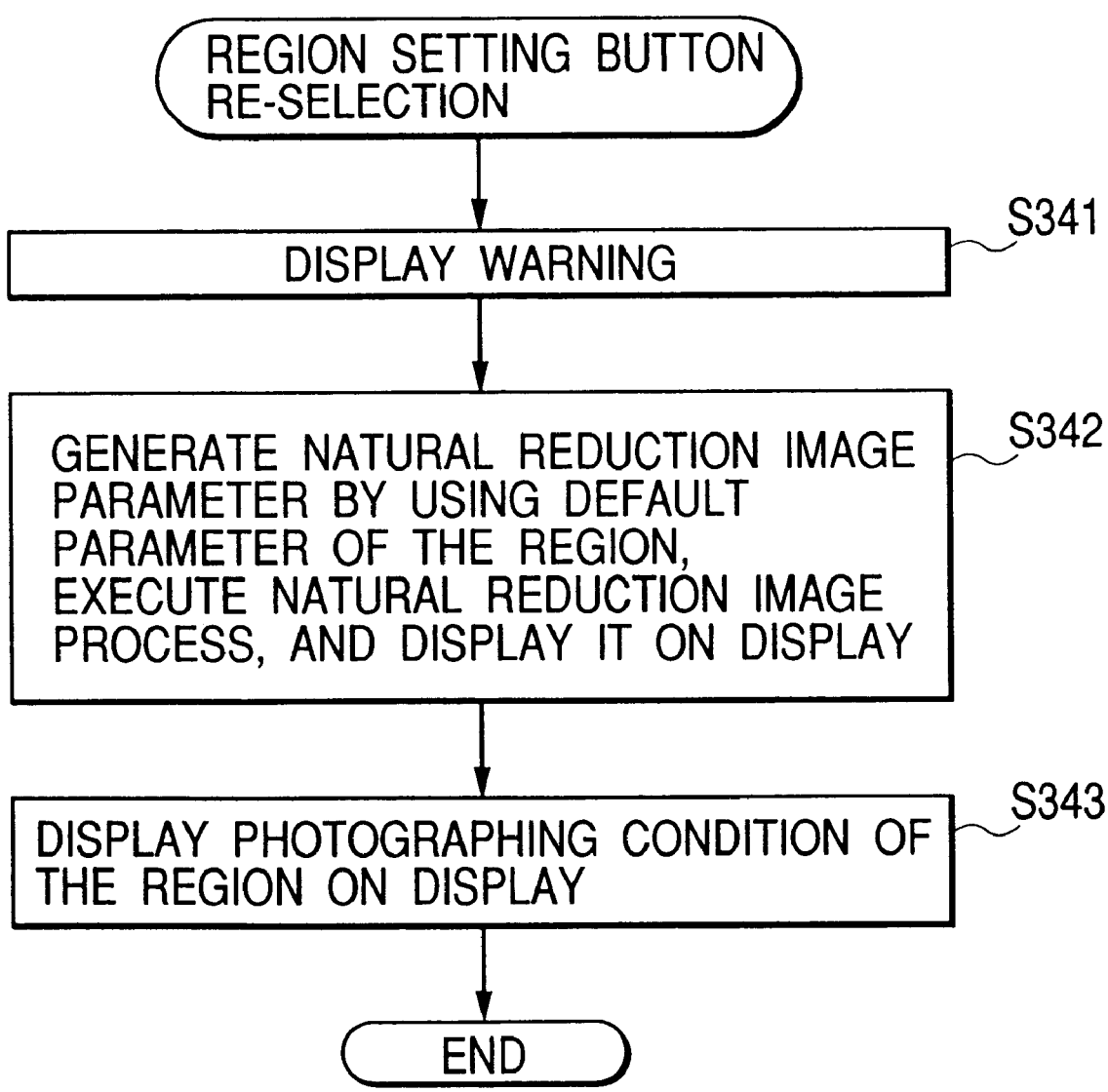

FIG. 21

| | |
|---|---|
| INSPECTION ATTRIBUTION | PATIENT ATTRIBUTION |
| | INSPECTION SPECIFIC ATTRIBUTION |
| | THE NUMBER OF PHOTOGRAPHED IMAGE |
| IMAGE ATTRIBUTION OF FIRST IMAGE | REGION NAME |
| | PHOTOGRAPHING CONDITION |
| | NATURAL IMAGE PROCESSING CONDITION |
| | NON-REVERSIBLE COMPRESSING COEFFICIENT |
| | NON-REVERSIBLE COMPRESSING RATIO |
| | NATURAL IMAGE FILE NAME |
| IMAGE ATTRIBUTION OF SECOND IMAGE | REGION NAME |
| | PHOTOGRAPHING CONDITION |
| | NATURAL IMAGE PROCESSING CONDITION |
| | NON-REVERSIBLE COMPRESSING COEFFICIENT |
| | NON-REVERSIBLE COMPRESSING RATIO |
| | NATURAL IMAGE FILE NAME |
| ⋮ | ⋮ |
| IMAGE ATTRIBUTION OF N-TH IMAGE | REGION NAME |
| | PHOTOGRAPHING CONDITION |
| | NATURAL IMAGE PROCESSING CONDITION |
| | NON-REVERSIBLE COMPRESSING COEFFICIENT |
| | NON-REVERSIBLE COMPRESSING RATIO |
| | NATURAL IMAGE FILE NAME |

FIG. 22

| QID | IMAGE PROCESS | TRANSFER 1 | TRANSFER 2 | TRANSFER 3 | TRANSFER 4 | ERASE | INSPECTION FILE NAME |
|---|---|---|---|---|---|---|---|
| 2329 | DONE | DONE | DONE | DONE | RUNNING (TID=1) | UNDONE | F02329.QUE |
| 2330 | RUNNING (TID=2) | UNDONE | UNDONE | UNDONE | UNDONE | UNDONE | F02330.QUE |
| 2331 | UNDONE | UNDONE | UNDONE | UNDONE | UNDONE | UNDONE | F02331.QUE |
| 2332 | UNDONE | UNDONE | UNDONE | UNDONE | UNDONE | UNDONE | F02332.QUE |
| 2333 | UNDONE | UNDONE | UNDONE | UNDONE | UNDONE | UNDONE | F02333.QUE |
| 2334 | UNDONE | UNDONE | UNDONE | UNDONE | UNDONE | UNDONE | F02334.QUE |

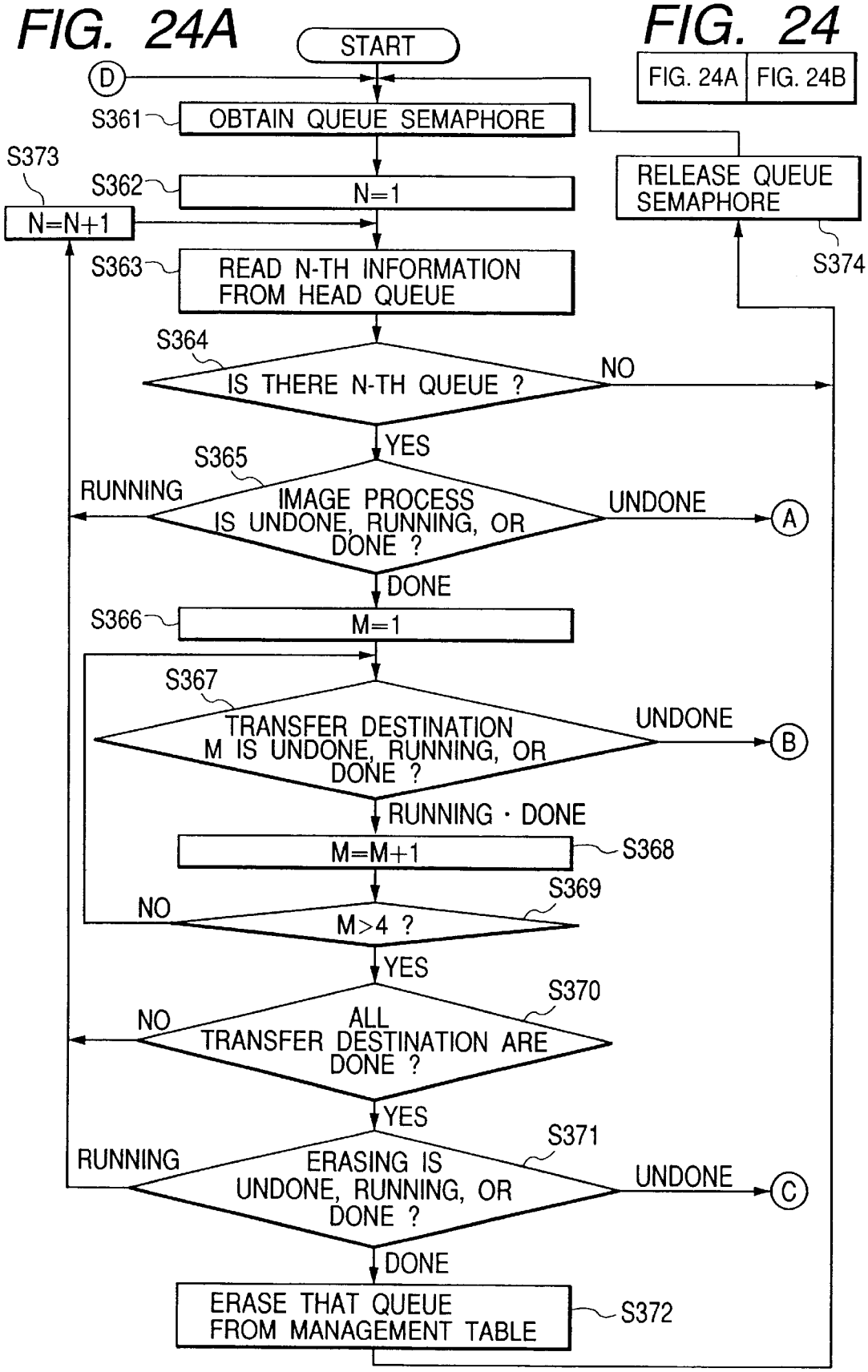

IMAGE PROCESS, IMAGE SENDING, IMAGE ERASING PROCESS

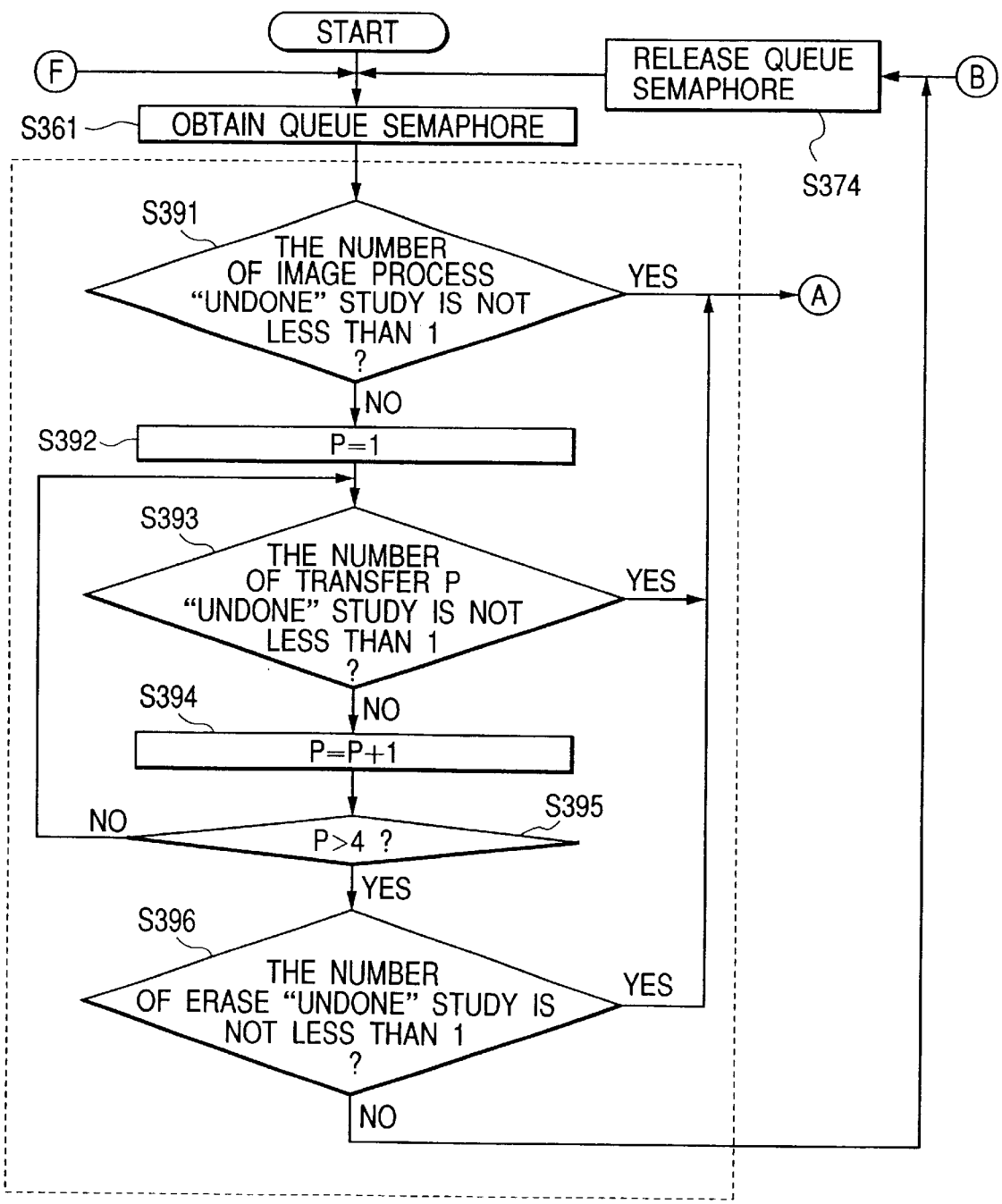

IMAGE PROCESS, IMAGE SENDING,
IMAGE ERASING PROCESS 2

IMAGE PROCESSING APPARATUS, IMAGE PROCESSING METHOD, AND RECORDING MEDIA

BACKGROUND OF THE INVENTION

1. Field of the Invention

The present invention relates to an image processing apparatus and method employed for an X-ray digital photographing apparatus, for example, in which image processing for a reduced image of an original image or correction processing for the original image are performed based on image processing conditions (parameters) set for each processing, and computer readable storage media for storing processing steps for implementing these processes.

2. Related Background Art

As a system for performing X-ray photography targeted for medical diagnosis, for example, there is frequently used a film screen system using photosensitive paper and X-ray photographing film in combination.

In this system, X-rays are transmitted to an object, thereby acquiring X-rays including internal information of the object; and the obtained X-ray is converted into visible light parallel to intensity of the X-rays by means of photosensitive paper, thereby causing an X-ray film (an X-ray photographing film) to be photosensitive. As a result, an X-ray image of the object is formed on the X-ray film.

In recent years, an X-ray digital photographing apparatus has been used. In this X-ray digital photographing apparatus, X-rays are converted into visible light parallel to intensity of the X-rays by means of a phosphor, the converted visible light is converted into an electric signal by means of a photosensitive converting element, and the converted signal is further digitized by means of an analog/digital converter.

Here, the above X-ray digital photographing apparatus is achieved so as to make an X-ray image visible immediately on a screen. Therefore, an operator such as X-ray technician or doctor responsible for diagnosis can check positioning of an X-ray image or adjustment of image processing (such as brightness control of a photography image) immediately after photography.

For example, the operator specifies that image process parameters are changed while referring to an X-ray image displayed on the screen (an image in which image processing has been applied using preset image process parameters). Thereby, in the apparatus, image processing is performed for an X-ray image using the changed or specified image process parameters. This X-ray image after image processing is redisplayed on the screen. Thus, the operator specifies that image process parameters are changed until a desired image has been obtained. Then, the operator determines image process parameters when the displayed X-ray image on the screen (the image in which image processing has been applied using the changed or specified image process parameters) is judged as a desired image (i.e., when image processing is proper).

Thus, the operator specifies that image process parameters are changed while referring to the displayed X-ray image on the screen, thereby adjusting the X-ray image and determining the image process parameters. In this manner, a desired X-ray image is obtained.

However, in order to perform image processing using the changed or specified image process parameters by the operator, it is required to mount specific hardware for the image processing (a specific image processing board) in the apparatus or system.

Therefore, conventionally, although fast processing speed can be ensured by utilizing such specific image processing board, there has been a problem that the apparatus or system becomes costly.

In a general-purpose CPU governing an image processing apparatus, it is required to perform the above image processing by software. However, in this case, although cost reduction can be ensured, processing speed becomes much slower than that when the specific image processing board is utilized. In addition, a waiting time for changing or specifying image process parameters on the operator side becomes long.

SUMMARY OF THE INVENTION

The present invention has been achieved to eliminate the above mentioned disadvantages. It is an object of the present invention to provide an image processing apparatus capable of ensuring speedy processing and cost reduction.

In the view of such processing, as a first aspect of the present invention, there is provided an image processing apparatus comprising: generating means for reducing an original image based on reduction conditions, thereby generating a reduced image; image processing means for performing image processing for the reduced image based on a set first image processing condition; and image correcting means for performing image correction of the original image based on a set second image processing condition, the first and second image processing conditions are associated according to the reduction conditions.

Other objects and advantages besides these discussed above shall be apparent to those skilled in the art from the description of a preferred embodiment of the invention which follows. In the description, reference is made to accompanying drawings, which form a part thereof, and which illustrate an example of the invention. Such example, however, is not exhaustive of the various embodiments of the invention, and therefore, reference is made to the claims which follow the description for determining the scope of the invention.

BRIEF DESCRIPTION OF THE DRAWINGS

FIG. 18 is a view for illustrating image process parameters used in the above image processing;

FIG. 20 is a flow chart for illustrating processing during re-selection of the above site setting button;

FIG. 21 is a view for illustrating an image information file obtained after the completion of photography by means of the above X-ray image photographing apparatus;

FIG. 22 is a view for illustrating a queue table for managing each queue unit in the above task configuration;

DETAILED DESCRIPTION OF THE PREFERRED EMBODIMENTS

Hereinafter, embodiments of the present invention will be described with reference to the accompanying drawings.

First Embodiment

Figure 1:
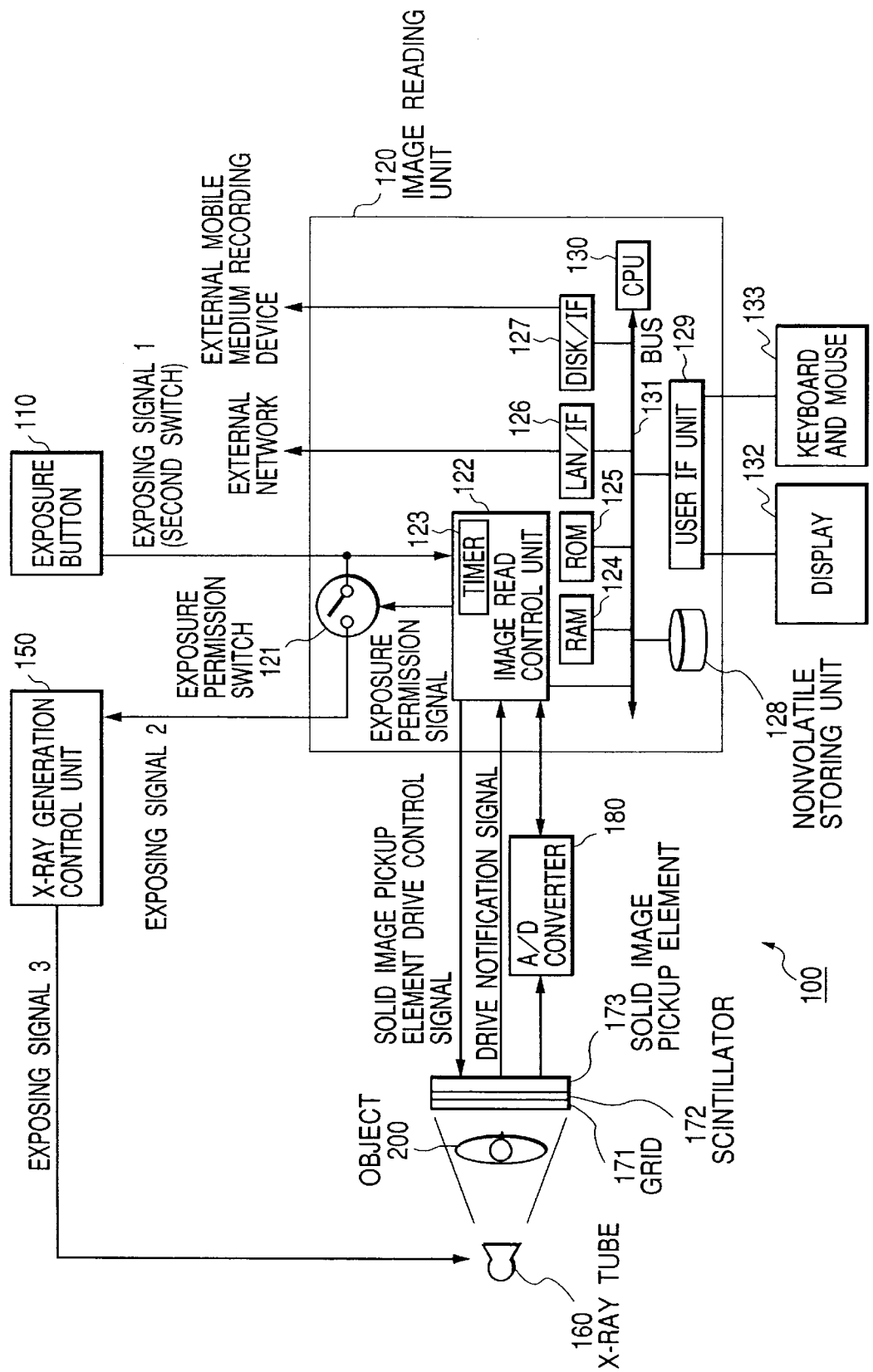
FIG. 1 is a block diagram depicting a configuration of an X-ray image photographing apparatus to which the present invention is applicable in a first embodiment.

The present invention is applicable to an X-ray image photographing apparatus 100 as shown in FIG. 1, for example.

This X-ray image photographing apparatus 100 is employed for X-ray photography for medial diagnosis. As shown in FIG. 1, there are provided an exposure button 110 serving as a trigger for generating X-rays; an X-ray tube 160 for generating X-rays; an X-ray generation control unit 150 for controlling the X-ray tube 160 in accordance with an exposing signal 1 generated by the exposure button 110; a solid image pickup element 173 in which the X-rays from the X-ray tube 160 transmits an object 200 and is incident; and an analog/digital (A/D) converter 180 for digitizing an output of the solid image pickup element 173, a grid 171 and a scintillator 172 being provided on the object 200 side of the solid image pickup element 173.

In addition, the X-ray image photographing apparatus 100 is provided with an image reading unit 120 for supplying an exposing signal 2 to an X-ray generation control unit 150 in accordance with a drive notification signal from the solid image pickup element 173 and performing predetermined processing for an image signal from the A/D converter 180.

A display 132 and an operating unit 133 consisting of a keyboard and a mouse or the like each are connected to the image reading unit 120.

The image reading unit 120 comprises an image read control unit 122 having a timer 123; a RAM 124 including a work area or the like; a ROM 125 for storing data for executing various processes, processing programs or the like; a LAN/IF unit 126 that is an interface with an external network (LAN); a DISK/IF unit 127 that is an interface with an external portable media recording apparatus; a user IF unit 129 that is an interface with a user, a display 132 and an operating unit 133 being connected thereto; a nonvolatile storing unit 128 such as hard disk; and a CPU 130 governing operation control of the entire apparatus each connected on a bus 131 and structured of receiving data mutually.

In addition, the image reading unit 120 is provided with an exposure permission switch 121 for supplying an output of the image read control unit 122, so that the above exposing signal 2 from this exposure permission switch 121 is supplied to an X-ray generation control unit 150.

Now, a series of operations of the above mentioned X-ray image photographing apparatus 100 will be described.

First, an operator such as X-ray technician or doctor and the like places an object 200 (patient) of interest between the solid image pickup element 173 and the X-ray tube 160. Next, the operator operates a region setting button for setting a region of interest of the object 200. This region setting button is provided on a display screen of the display 132, as described later in detail.

When such operation is recognized by the CPU 130 inside of the image reading unit 120, the image read control unit 120 is controlled by the CPU 130. Using a solid image pickup element driving control signal (hereinafter, referred to as "a driving control signal"), a voltage is applied to the solid image pickup element 173. Then, preparation is done such that an image input (X-ray incidence via the object 200) is made for the solid image pickup element 173. At the same time, the timer 123 provided inside is started. Thereafter, from the solid image pickup element 173, a drive notification signal indicating whether or not X-ray imaging is enabled is outputted to the image read control unit 122.

On the other hand, the exposure button 110 serves as a trigger for generating X-rays. The exposing signal 1 generated by this exposure button 110 is temporarily inputted to the image read control unit 122 in the image reading unit 120.

The image read control unit 122 checks whether or not imaging is enabled when the control unit receives X-rays by the drive notification signal from the solid image pickup element 173; and generates an exposure permission signal when imaging is enabled. This exposure permission signal is generated by turning ON the exposure permission switch 121 and causing the exposing signal 1 to be conductive to an exposing signal 2.

The exposure permission switch 121 consists of a switch called a second switch of the exposure button 110. When the exposure permission switch 121 is turned ON, the second switch is available in use. Therefore, the exposure permission switch 121 is turned ON, and when the second switch is pressed by the operator, the exposing signal 2 is generated.

The thus outputted exposing signal 2 from the exposure permission switch 121 is supplied to the X-ray generation control unit 150.

The X-ray generation control unit 150 generates an exposing signal 3 to an X-ray tube 160 by the exposing signal 2 from the exposure permission switch 121 when preparation for X-ray exposure with the X-ray tube 160 is done. Thereby, X-rays are generated from the X-ray tube 160.

The X-rays generated from the X-ray tube 160 (its transmitted rays) are incident to the solid image pickup element 173 sequentially via the grid 171 and the scintillator 172. The incident light is photoelectric-converted at this solid image pickup element 173, and an electric signal (an X-ray image signal) of the object 200 is obtained.

An A/D converter 180 reads out an X-ray image signal obtained by the solid image pickup element 173 and digitizes the signal, and supplies it to the image read control unit 122 of the image reading unit 120.

The image read control unit 122, as described above, an operation control of which is managed by the CPU 130, temporarily spreads X-ray image data from the A/D converter 180 on a RAM 124, and performs predetermined various processes for the data described later.

Next, a primarily featured flow and configuration of the above mentioned series of operations will be specifically described.

[Operation Caused by the Operator and Operation of the Apparatus in Accordance Therewith]

Operations to be performed by the operator for photography include an operation for a region setting button for setting a region of interest. The region setting button is provided on the display screen of the display 132.

Figure 2:
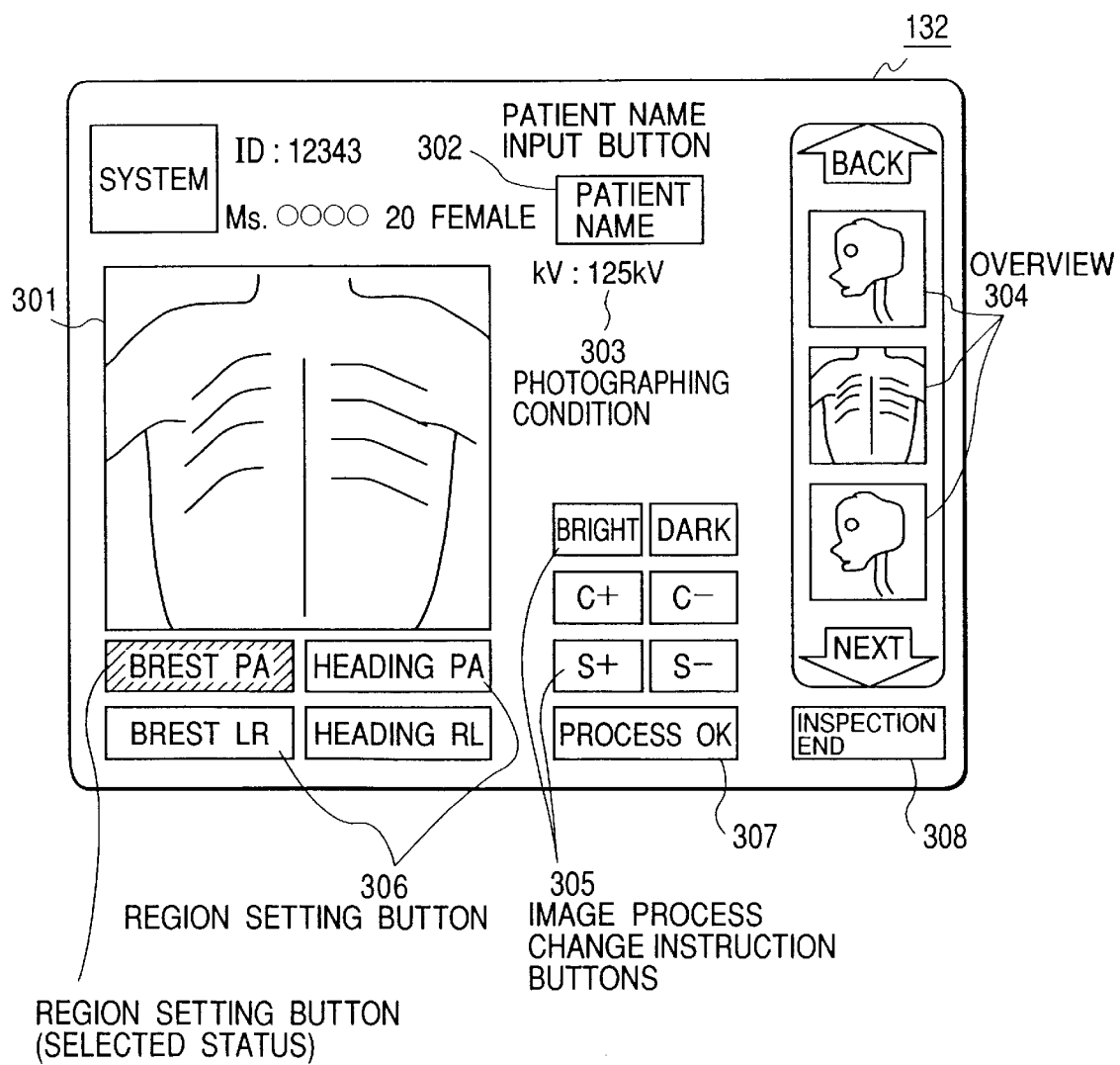
FIG. 2 is a view for illustrating a screen configuration of a display in the above X-ray image photographing apparatus.

FIG. 2 shows a state on the display screen of the display 132. As shown in FIG. 2, the screen of the display 132 is provided with the above mentioned region setting buttons 306 ("breast part PA", "head part PA", "breast part LR", and "head part RL"); an image display 301 for displaying a photographed, obtained X-ray image; an input button 302 for information (information of a patient targeted for photographed" of an object 200 ("patient name"); a photographing condition display 303 for displaying photographing conditions ("kV: 125 kV"); an overview display 304 for reducing and displaying a photographed, obtained X-ray image; an image process change instruction buttons 305 ("bright" "dark", "C+", "S+", "C−", and "S−"); a processing OK button 307 ("processing OK"), and an inspection end 308 ("end of examination") or the like.

The operator selects a region setting button corresponding to a region of interest in an object 200 in order to photograph the object 200 (patient). For example, by operating the mouse of the operating unit 133, the operator selects a desired one of the region setting buttons such as "breast part PA", "head part PA", "breast part LR", and "head part RL", and clicks it. FIG. 2 shows a state when the region setting button "breast part PA" is selected (a shaped part). At this time, if the operator has selected an incorrect region setting button, the operator can select another region setting button, thereby enabling re-selection.

Such region setting button selection operation is read by the CPU 130 of the image reading unit 120, and a default value for the image process parameters of an X-ray image to be collected by photography is determined by controlling the CPU 130 in accordance with the read operation. Then, each of processes is executed, which include setting of a region name for an X-ray image; default X-ray tube setting; driving of the solid image pickup element 173 using a driving control signal; and starting of a timer 123 in the image read control unit 122 or the like.

Figure 3:
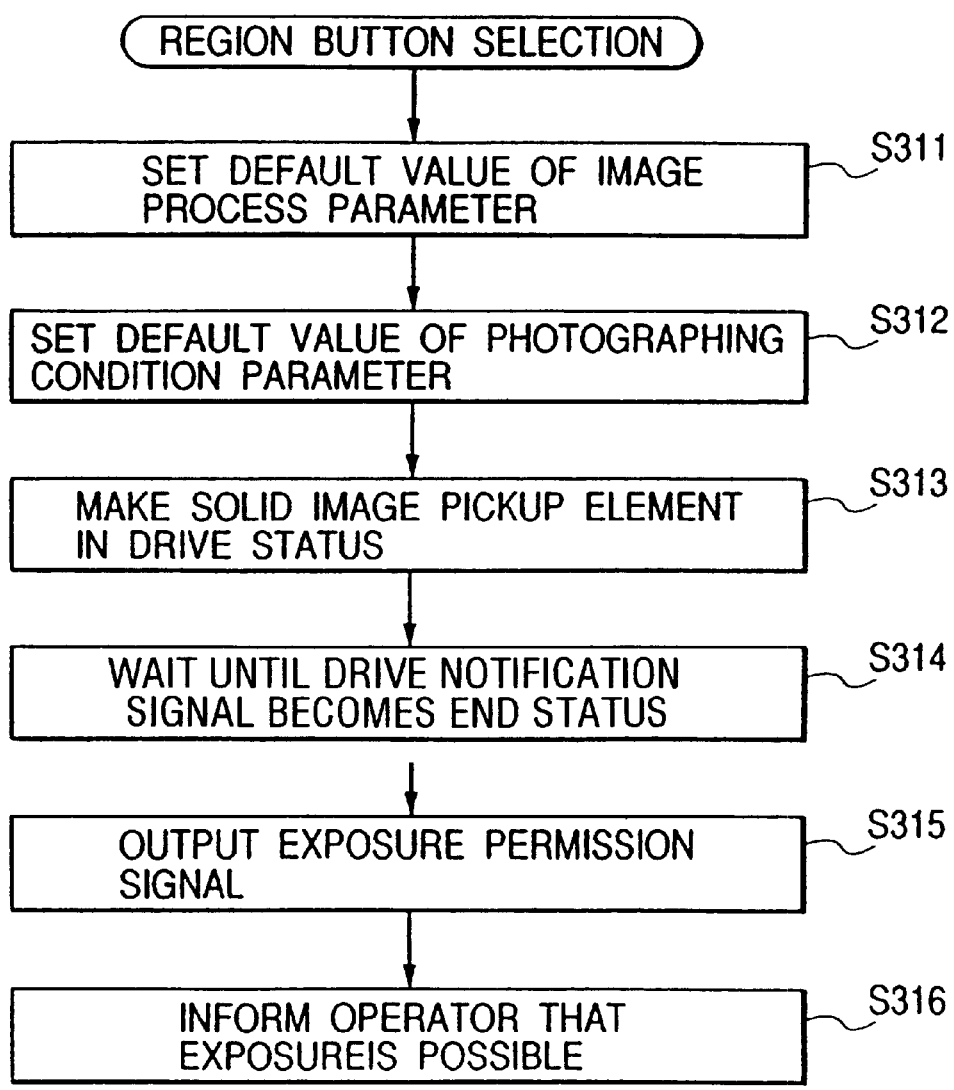
FIG. 3 is a view for illustrating an operation in accordance with an operation of a region setting button provided on a screen of the above display.

FIG. 3 shows a flow chart of an operation of the apparatus in accordance with an operation of the above mentioned region setting button 306.

When the operator selects a region setting button as described above, the image reading control 122 determines a default value for the image process parameters for image processing and a default value for the photographing condition parameters or the like (steps S311 and S312).

Next, the image read control unit 122 supplies a driving control signal to the solid image pickup element 173, and starts the timer 123. Thereby, the solid image pickup element 173 is driven (step S313).

Then, after the solid image pickup element 173 waits for a state (an end status) in which an image signal with its stable image quality can be outputted, it supplies a drive notification signal to the image read control unit 122. The image read control unit 122 recognizes that the solid image pickup element 173 is completed by this drive notification signal (step S314).

The image read control unit 122 generates an exposure permission signal. Thereby, the exposure permission switch 121 is turned ON, so that a second switch of the exposure button 110 can be utilized (step S315).

Thereafter, to inform the operator that exposure is possible, the image read control unit 122 supplies a signal indicating the fact to the display 132 via a user IF unit 129. The display 132 receiving this signal changes a background color of the display screen from "blue" to "green" (step S316).

Therefore, when the background color is changed to "green" on the display screen of the display 132, the operator recognizes "photography enable", and operates the exposure button 110. In this manner, the exposing signal 2 is outputted from the exposure permission switch 121 (second switch), and subsequently, photography for the object 200 is started as described above.

In addition, the operator performs an operation for inputting information (information of a patient targeted for photography) concerning the object 200 to be photographed in addition to the above-mentioned region setting button 306.

Specifically, the operator first clicks an input button 302 on the display screen of the display 132 (refer to FIG. 2 above) by using the mouse of the operating unit 133.

Such operation is read by the CPU 130 of the image reading unit 120, and additional patient information window appears on the display 132 by controlling the CPU 130 in accordance with the read information.

Then, the operator inputs information such as patient name, patient ID, date of birth, age or the like by using the mouse and keyboard of the operating unit 133.

The above mentioned input operation of "patient name" is possible before and after performing selection operation of the region switch or after collecting an image after photography, as long as a patient targeted for photography is under photography.

That is, an inspection end 308 provided on the display screen of the display 132 is operated, irrespective of a sequence of input operation of "patient name" as long as an examination consisting of a plurality of photographing processes regarding a target patient is not ended. Thereby, a patient with its serious conditions can be photographed in case of an emergency such that the operator does not have enough time for inputting a "patient name".

[Timer 123 of the Image Read Control Unit 122 and Operation Caused by the Timer]

The timer 123 provided in the image read control unit 122 is designed so that counting is commenced (started) from a count value "0" every time the operator selects a region setting button on the display screen of the display 132 by means of the above switch S313 of FIG. 3. The count value of this timer 123 is supervised by means of the image read control unit 122.

The image read control unit 122 supervises the count value of the timer 123. In the case where the count value indicates a specified time, for example, 10 minutes, the control unit stops supply of the driving control signal to the solid image pickup element 173, and stops supply of the exposure permission signal to the exposure permission switch 121. In this manner, the driving state of the solid image pickup element 173 is released, and the exposure permission switch 121 is turned OFF.

In addition, in this case, to report "photography disable" to the operator, the image read control unit 122 supplies a signal indicating the fact to the display 132 via a user IF unit 129. The display 132 receiving this signal set to a non-selection state a selection state of the selected region setting button by the operator, and returns its background color from "green" to "blue".

Through such operation, the solid image pickup element 173 can be prevented from being always driven inside the device, and as a result, the solid image pickup element 173 can be prevented from being degraded.

[Task Configuration of the Image Reading Unit 120]

Figure 4:
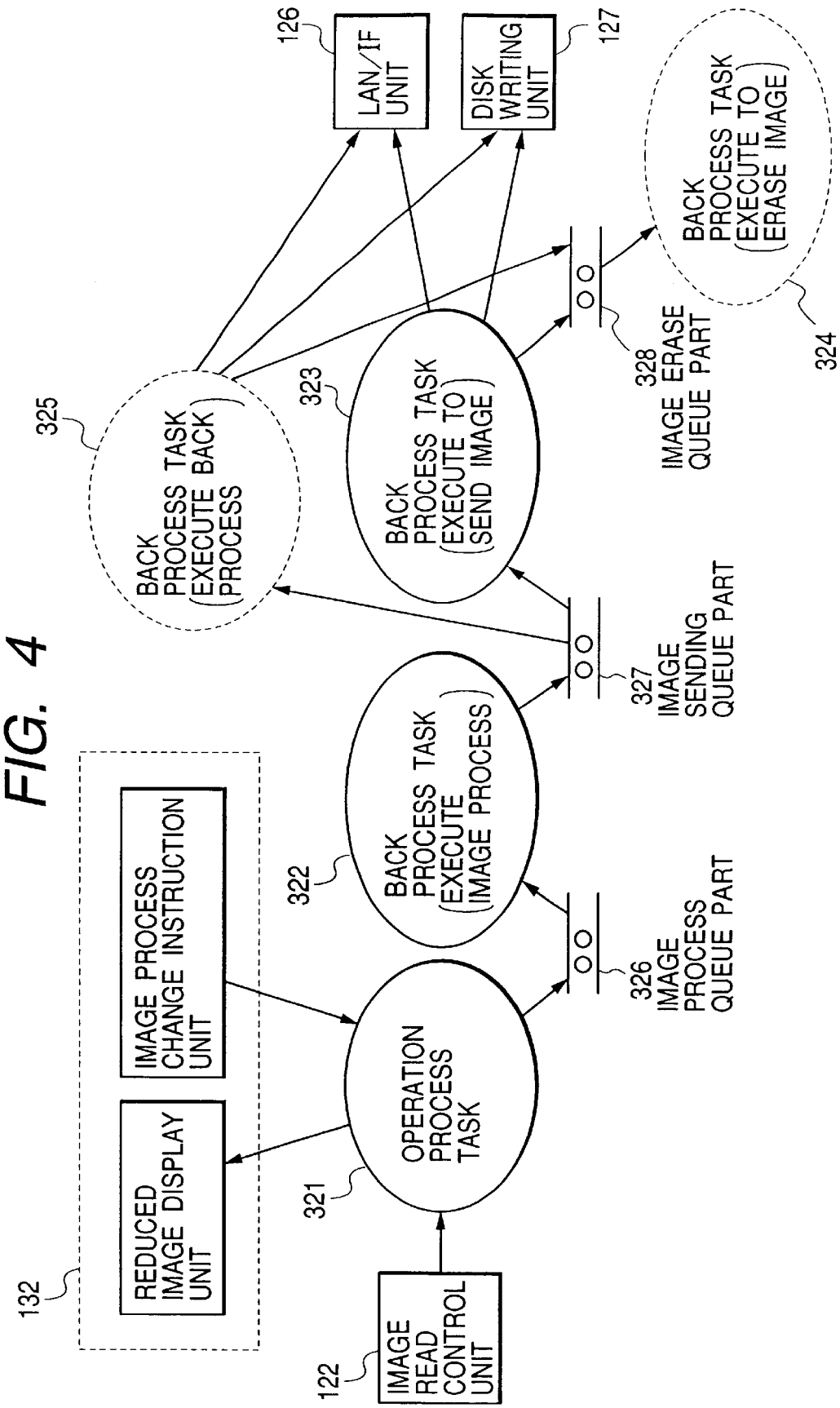
FIG. 4 is a view for illustrating a task configuration of an image reading unit in the above X- ray image photographing apparatus.

FIG. 4 shows a task configuration of the image reading unit 120. A plurality of tasks 321 to 325 as shown in FIG. 4 are achieved so as to operate in parallel by time division by means of the CPU 130. These tasks 321 to 325 have the functions as described below.

The operation process task 321 is a task for primarily performing processing based on a variety of operations of the operator to be performed on the display screen of the display 132.

The back process tasks 322 to 325 are tasks for performing processes such as image processing for X-ray images collected by photography, network transfer of X-ray images undergoing the image processing via the 1 unit 126 or external transfer to a large-scale portable disk via a DISK/IF unit 127, and deletion of the transferred X-ray images, as required. In addition, when an X-ray image is externally transferred, the image is transferred in non-reversible compression manner (for example, DCT using the JPEG method: Discrete cosine conversion) using a predetermined non-reversible compressing coefficient. These tasks perform this non-reversible compression process.

As described above, four back process tasks 322 to 325 are employed. One of the features is that four or more processes (jobs) can be executed by four or less tasks.

Specifically, by referring now to FIG. 4, there is shown a state in which four or more processes are executed by two back process tasks 324 and 325 (enclosed in a circle indicated by dashed line in the figure). The number of this operating tasks (tasks in an executable state) varies depending on when photographing operation is performed or not.

For example, when photographing operation is started by operation of the operator, two tasks, i.e., an operation process task 321 and a back process task 322, are placed in active state. After photographing operation is completed, if an operation for the next photography is not performed for one minute, for example (this time-out time can be additionally set on the setting panel), the number of active tasks at this time increases to three tasks, i.e., the operation process task 321, the back process task 322, and a back process task 323 or 325. In addition, when photographic operation is restarted by operation of the operator, the number of active tasks decreases to two tasks, i.e., the operation process task 321 and the back process task 322. Timing of this task decrease is not performed while processing is executed by these tasks without being completed. A task is decreased at the time when processing is completed.

As described above, when photographing operation is started by operation of the operator, the number of active tasks decreases, thus making it possible to perform background processing without impairing photographic operation.

In addition, an image process queue part 326 is provided between the operation process task 321 and the back process task 322 performing image processing. This image process queue part 326 provides a non-volatile first-in first-out mechanism for image-processing a generated X-ray image by photographing operation.

Still additionally, an image sending queue part 327 is provided between the back process task 322 performing image processing and the back process task 323 performing image transmission. This image sending queue part 327 provides a non-volatile first-in first-out mechanism for transmitting an X-ray image of which the image processing is ended by the back process task 322 performing image processing.

Further, an image erase queue part 328 is provided between the back process task 323 performing image transmission and the back process task 324 executing image deletion. This image erase queue part 328 provides a non-volatile first-in first-out mechanism for erasing an X-ray image of which all image transmissions are ended.

As described above, by providing the non-volatile first-in first-out mechanism, relatively time-consumable image processing can be performed parallel to image transmission, thus making it possible for the operation process task 321 requiring a fast response to smoothly perform its processing. In addition, while an image is processed by the back process task 322 or an image is transmitted by the back process task 323, even if operation of the apparatus ends for any reason (such as power OFF), an image obtained by photography is not lost.

Management of the above image process queue part 326, the image sending queue part 327, and the image erase queue part 328 will be described in detail.

[Image Processing at the Image Reading Unit 120]

The present apparatus is primarily featured by image processing using image process parameters at the image reading unit 120.

As described with respect to a series of operations discussed above, when an X-ray occurs with the X-ray tube 160 after the exposure button 110 (second switch) is pressed by the operator, the X-ray is incident to the solid image pickup element 173. The thus obtained X-ray image signal by the solid image pickup element 173 is supplied as X-ray image data (digital) to the image read control unit 122 of the image reading unit 120 via an A/D converter 180.

The image read control unit 122 generates a reduced image 301 shown in FIG. 2, and processes a natural image according to determined image adjustment parameters by the reduced image 301.

Figure 5:
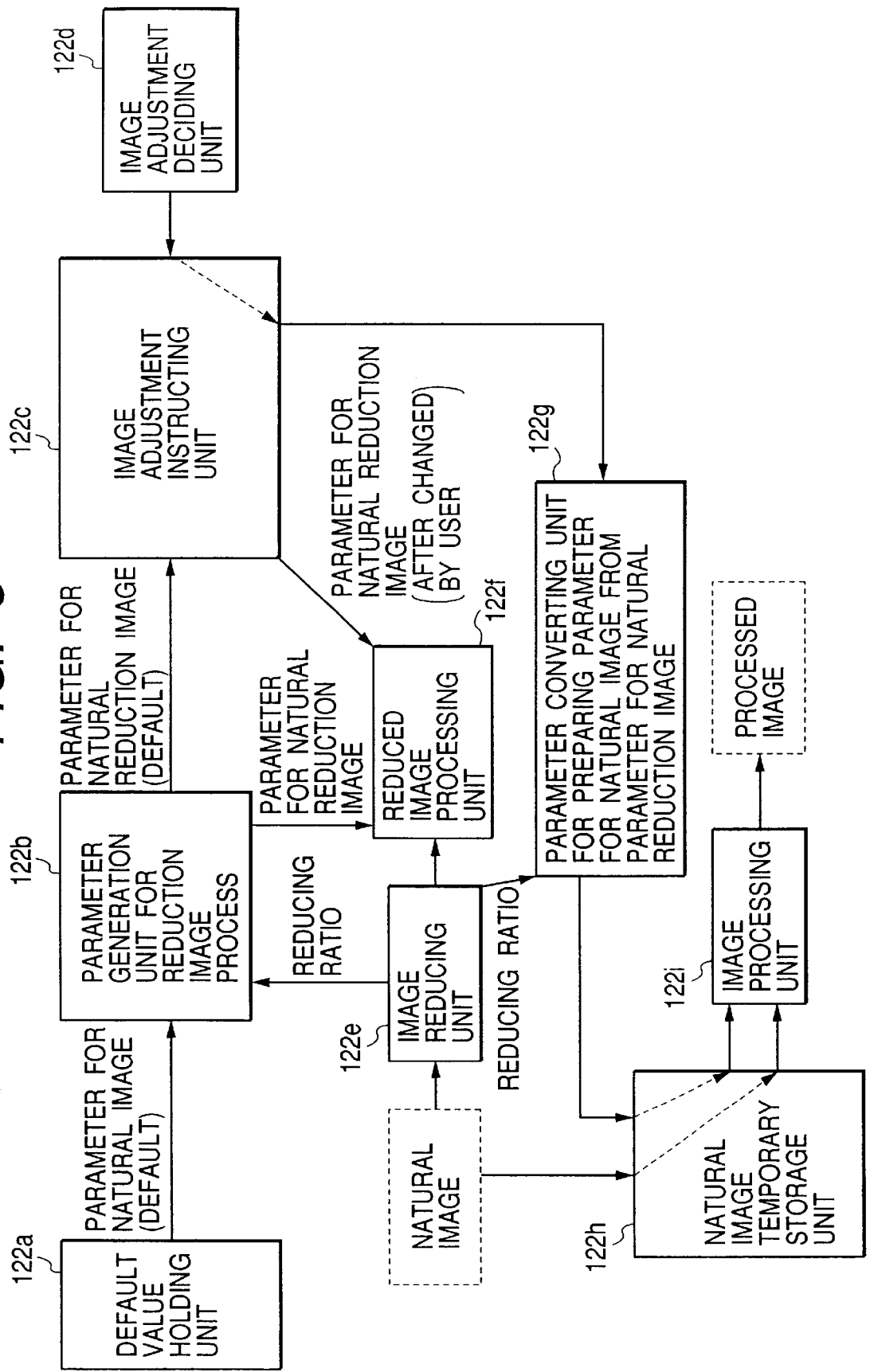
FIG. 5 is a block diagram depicting an internal configuration of an image read control unit of the above image reading unit.

FIG. 5 shows an internal configuration of the image read control unit 122. By referring to FIG. 5, a generation process of the reduced image 301 at the image read control unit 122 will be described.

A parameter generating unit 122b for reduced-image processing reads out a default value that is a recommended image adjustment parameter from a default value holding unit 122a. This default value is an image adjustment parameter for a natural image. Therefore, the parameter generating unit 122b for reduced-image processing converts the above default value to a parameter for a reduced natural image based on a predetermined reduction ratio employed at an image reducing unit 122e described later.

The image reducing unit 122e converts a natural image to a reduced natural image based on a predetermined reduction ratio. For example, an image reduction process and a sampling process are performed such that the size of the reduced image is 12-bit data with horizontal 336 pixels and vertical 336 pixels (reduction of 1/8). Hereinafter, natural image data undergoing these processes is referred to as "natural reduction image data" (display image data).

The above natural image is temporarily stored in a natural image temporary storage unit 122h.

The reduced image processing unit 122f applies image processing based on parameters for reduced natural images obtained at the parameter generating unit 122b for reduced-image processing to reduced natural image data obtained at the image reducing unit 122e, thereby converting the reduced natural image data to a reduced image 301. This reduced image 301 obtained at the reduced image processing unit 122f is displayed.

The user checks adjustment results based on the displayed reduced image 301, and performs image adjustment until desired adjustment results have been obtained. An instruction from the user regarding readjustment at this time is inputted to the image adjustment instructing unit 122c via the user I/F unit 129 shown in FIG. 1.

The image adjustment instructing unit 122c corrects parameters for reduced natural images employed for the displayed reduced image 301, i.e., parameters for reduced natural images employed for image processing at the reduced image processing unit 122f according to the user instruction.

Therefore, at the reduced image processing unit 122f, a reduced image is generated according to parameters for corrected, reduced images from the image adjustment instructing unit 122c, and is displayed. The parameters for reduced natural images at this time is held at the image adjustment instructing unit 122c.

In addition, a natural image is processed as follows according to the determined image adjustment parameters by the reduced image 301.

In the case where desired adjustment results are obtained with the above mentioned, reduced image 301, an instruction from the user for determining the image adjustment is inputted to the image adjustment deciding unit 122d via the user I/F unit 129 shown in FIG. 1.

The image adjustment deciding unit 122d supplies to a parameter converting unit 122g parameters for natural reduction images held at the image adjustment instructing unit 122c, i.e., parameters for reduced natural images when desired adjustment results were obtained.

The parameter converting unit 122g generates parameters for natural images based on parameters for natural reduction images from the image adjustment deciding unit 122d.

An image processing unit 122i performs image processing using parameters for natural images obtained at the parameter converting unit 122g with respect to natural images stored in the natural image temporary storing unit 122h, and generates images after processing.

Next, determination of image process parameters at the above mentioned image read control unit 122 will be specifically described.

Now, (1) an irradiation field recognition process, (2) an image enhancement process, and (3) a gradation conversion process will be described before description of determination of image process parameters, since image processing using image process parameters assumes that these three processes are executed in order.

(1) Irradiation Field Recognition Process

"Irradiation field recognition process" is a routine for extracting an image irradiation field area. The irradiation field area obtained by this routine is utilized for determination of density parameters at gradation conversion process to be performed at a subsequent stage. In addition, this area is utilized as cutout information to be transferred by cutting out an image portion required for network transfer.

Figure 6:
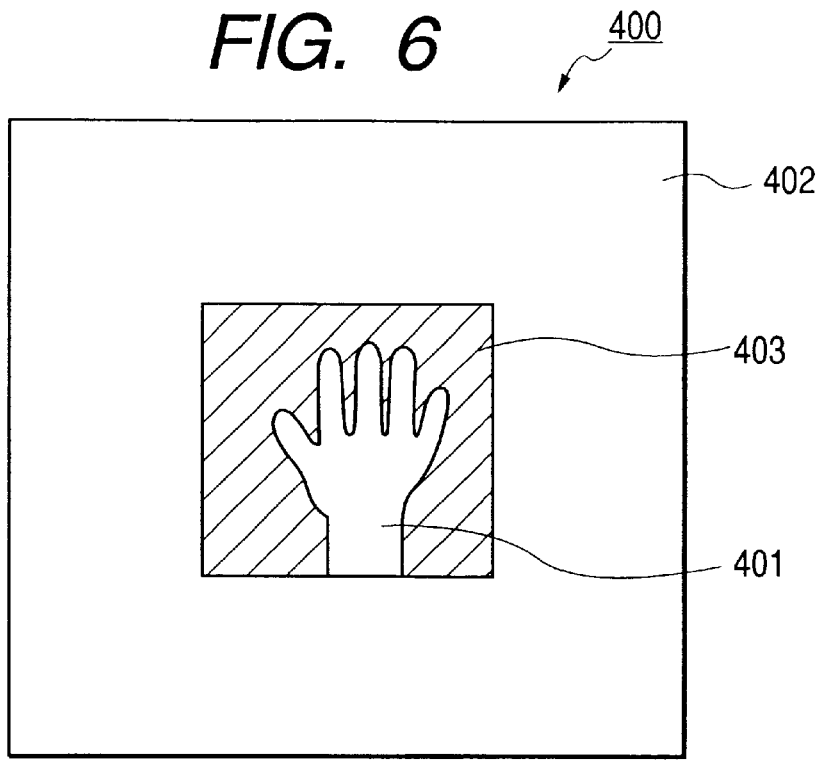
FIG. 6 is a view for illustrating an image with irradiation collimating in an irradiation field recognition process employed as image processing of the above image reading unit.

Specifically, in X-ray photography, as shown in FIG. 6, "radiation collimating" for irradiating only a required region 403 is performed to prevent scattering from an unwanted region 402 and lowering of contrast in a photography region 400 of an object 401. In the case where predetermined image processing is performed for the thus photographed and obtained X-ray image, image process parameters are determined from distributions of the density value of an image in an irradiated region, and the image processing is performed based on the image process parameters.

At this time, in a region of interest, when an unwanted region is irradiated without a region of interest being limited, unwanted image information, so-called, an region outside the region of interest may be used for determining image process parameters.

When image process parameters are determined, an irradiated region (an irradiation field area) is extracted, and image process parameters are determined using image information of only the region of interest of the irradiation field area.

Methods for extracting an irradiation field area include differentiating an image density value, thereby determining an end (an irradiation end) of the irradiation area from the differentiated value; and when a region part of the field outside the irradiation area is assumed, approximating the field region part by a primary approximation Equation, thereby determining an irradiation end from a difference between the approximated value and an actual density value.

Figure 7:
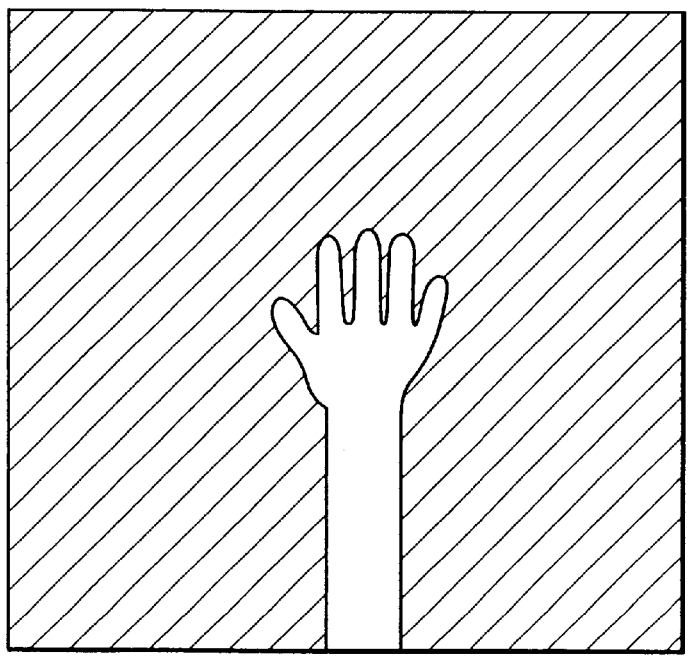
FIG. 7 is a view for illustrating an image without irradiation collimating in the above irradiation field recognition process.

These methods assumes that an image is photographed and obtained by performing the above mentioned irradiation collimating. Therefore, as preprocessing for implementing such methods, it is required to determine whether an X-ray image targeted for processing is an image photographed and obtained by performing irradiation collimating (an image with irradiation collimating or an image as shown in FIG. 6) or not (an image without irradiation collimating, for example, an image as shown in FIG. 7).

Figure 8:
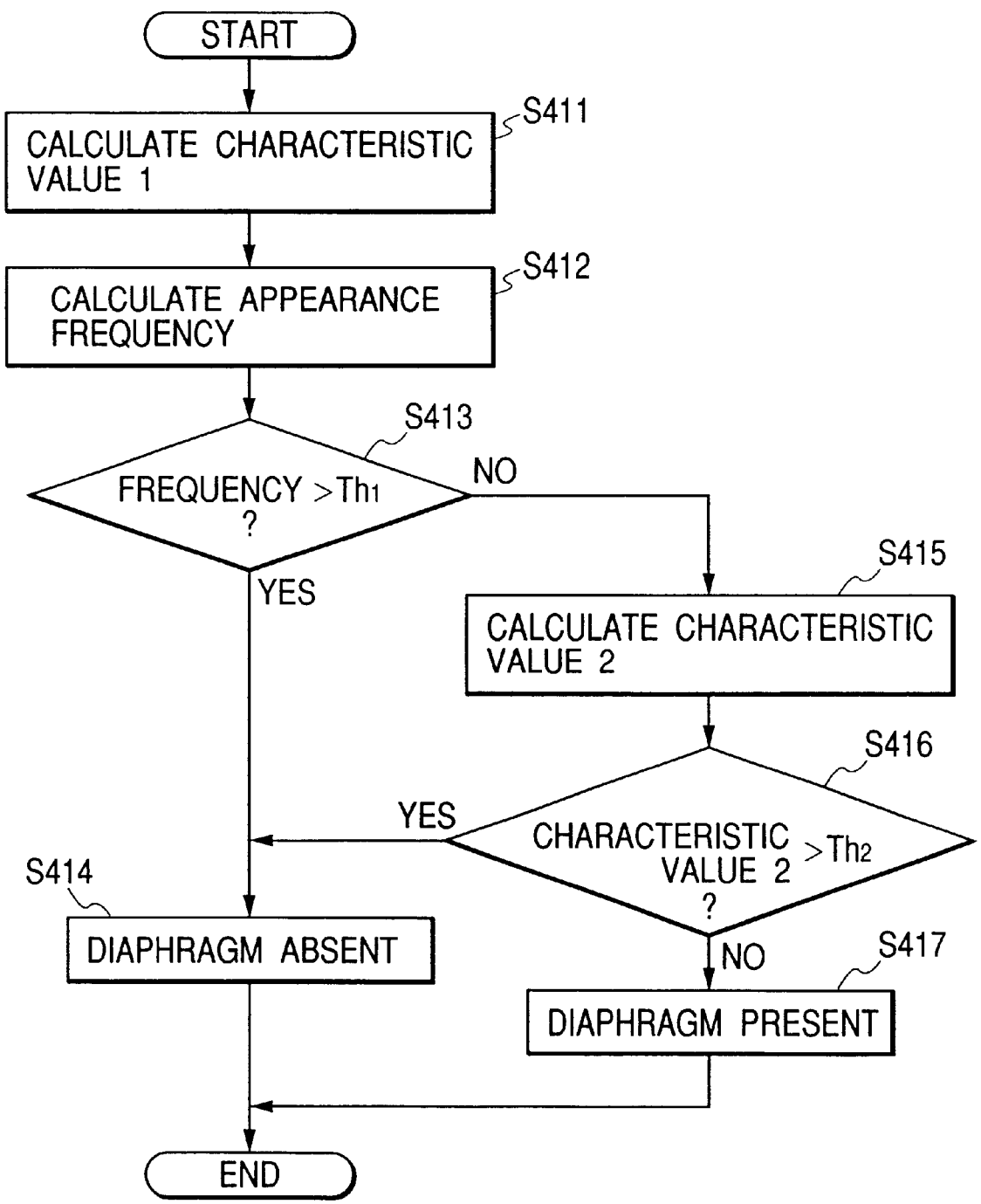
FIG. 8 is a flow chart for illustrating the above irradiation field recognition process.

There is a variety of methods for determining the presence or absence of irradiation collimating. As an example, a method for determining images according to a flow chart shown in FIG. 8 will be described.

Figure 9:
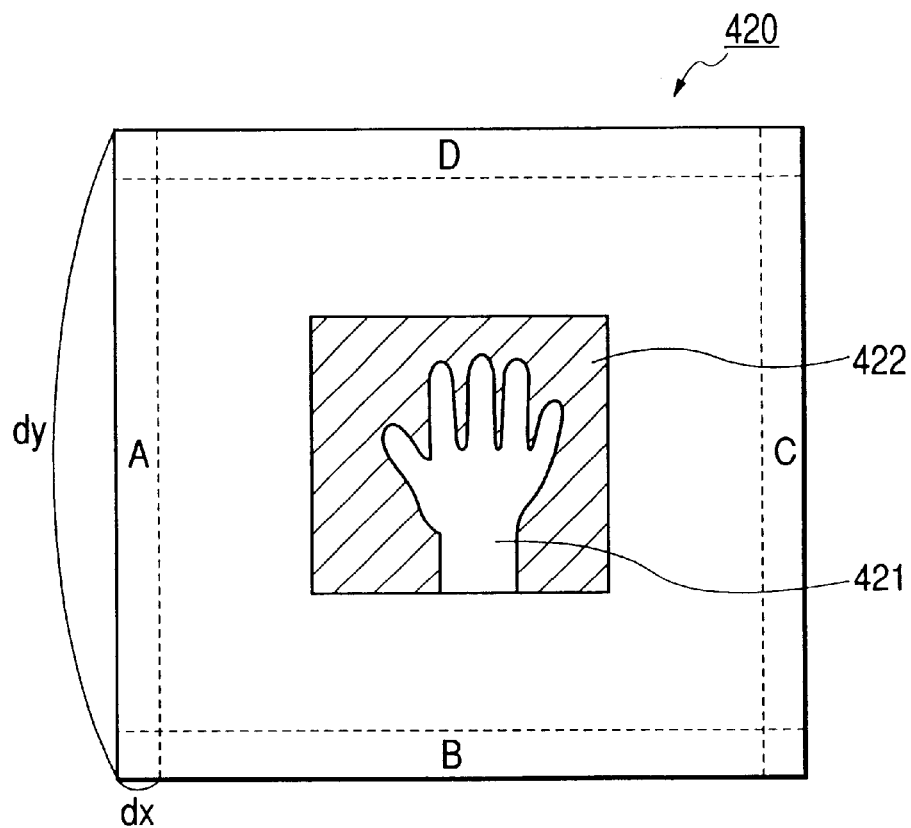
FIG. 9 is a view for illustrating a computing process of appearance frequency of density values at an image end in the above irradiation field recognition process.

For example, in the case where the presence or absence of irradiation collimating of an X-ray image 420 as shown in FIG. 9 is determined (in the figure, reference numeral 421 designates an object, and reference numeral 422 designates an irradiation field area.), the maximum value of the entire X-ray image 420 is computed as a first characteristic value S1 (step S411).

The maximum value is an upper part (for example, 5% point) of the accumulation histogram of the entire X-ray image 420.

The above maximum value sorts the density value of the entire X-ray image 420, for example, without being limited to the upper part of the accumulation histogram of the entire X-ray image 420, and may be employed as the upper part of the sorted value.

Next, a certain proportion of the first characteristic value S1 computed in step S411, for example, the appearance frequency of the density value of 90% or more at an image end (a left end) A (refer to FIG. 9) is computed (step S412).

An image end A is defined as a region of "dx" in horizontal width and "dy" in vertical width.

Then, it is discriminated as to whether or not the computed appearance frequency in step S412 is greater than a certain value Th1 (step S413).

As a result of this discrimination, when the appearance frequency is greater than Th1, it is judged as an X-ray image 420 without irradiation collimating (step S414), and this process is ended.

On the other hand, as a result of discrimination of step S413, when the appearance frequency is not greater than Th1, it is temporarily judged as an X-ray image 420 with irradiation collimating.

[Equation 1]

$$S_2 = \sqrt{\int_0^{dy} \int_0^{dx} (f(x, y) - \overline{f}(x, y))^2 \, dx \, dy} \quad (1)$$

$$\overline{f}(x, y) = \frac{\int_0^{dy} \int_0^{dx} f(x, y) \, dx \, dy}{\int_0^{dy} \int_0^{dx} dx \, dy}$$

As shown in the above Equation (1), a standard deviation value S2 of a density value f (x, y) of an image end A is computed, and the standard deviation value S2 is defined as a second characteristic value S2 (step S415).

Next, it is discriminated as to whether or not the calculated second characteristic value S2 in step S415 is a certain value Th2 (step S416).

As a result of this discrimination, when the second characteristic value S2>Th2, it is judged as an X-ray image 420 without irradiation collimating (step S414), and this process is ended.

On the other hand, as a result of discrimination in step S416, when the second characteristic value S2 is not greater than Th2, it is judged as an X-ray image 420 with irradiation collimating (step S417), and this process is ended.

Hereinafter, the above mentioned processing steps are performed for the lower end B, right end C, and upper end D of the X-ray image 420 similarly.

As described above, in this image judgment method, it is judged as to whether an image with or without irradiation collimating is produced from the appearance frequency of the density value determined from the maximum value of the entire X-ray image 420. Therefore, this image judgment method is used, thereby making it possible to perform stable judgment even for an image of which the object 421 is included in an end of the irradiation field area 422.

In addition, in the case where it is judged as an image with irradiation collimating in step S413, a standard deviation is computed as the second characteristic value S2 from image ends (A to D). Based on this standard deviation, it is further judged as to whether an image with or without irradiation collimating is produced; and even if the object 421 covers the entire image ends (A to D), stable judgment can be performed.

In the above mentioned image judgment method, as shown in the above Equation (1), the standard deviation value of density value f (x, y) of the image ends is computed as the second characteristic value S2.

[Equation 2]

$$S_2 = \frac{\sqrt{\int_0^{dy} \int_0^{dx} (f(x, y) - \overline{f}(x, y))^2 \, dx \, dy}}{\overline{f}(x, y)} \quad (2)$$

As shown in Equation (2), the standard deviation value of the density value f (x, y) of the image ends may be defined as the second characteristic value S2 by computing a normalized value by an average value of the density value f (x, y) of the image ends.

Therefore, by using such method, stable judgment can be performed even if there is a less radiation quantity without being influenced by intensity of the radiation quantity or even if the object 421 covers the entire image ends (A to D).

Figure 10:
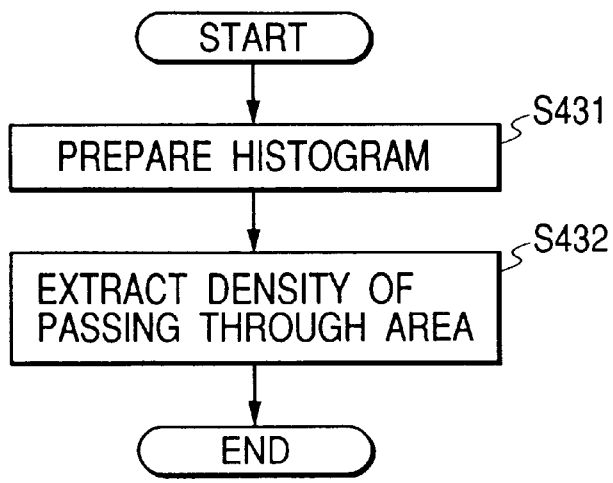
FIG. 10 is a flow chart for illustrating a characteristic value computing process in the above irradiation field recognition process.
Figure 11:
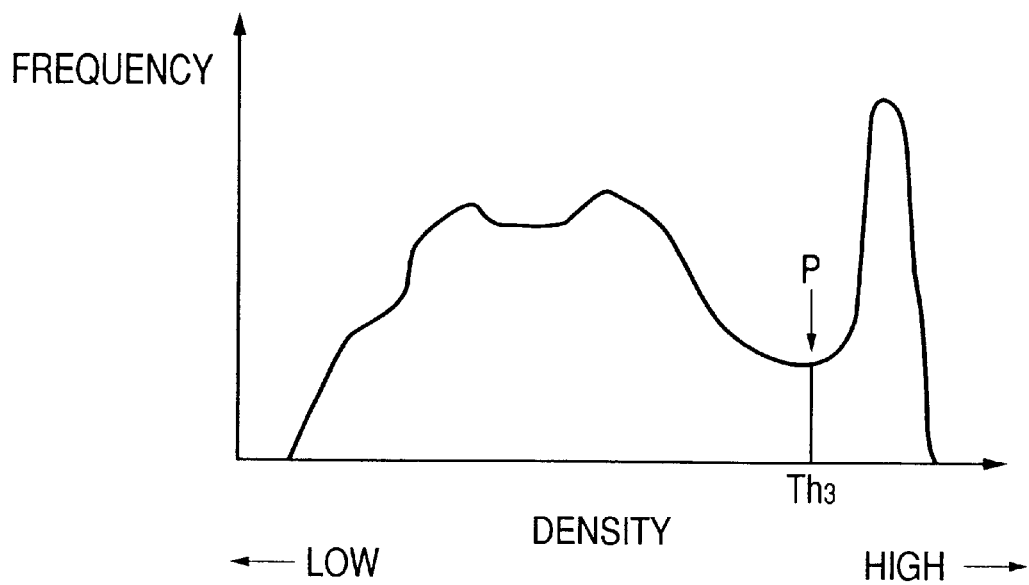
FIG. 11 is a view for illustrating a density value histogram obtained by the above characteristic value computing process.

In addition, the first characteristic value S1 may be computed from the density value histogram. In this case, in step S411 of FIG. 8, as shown in FIG. 10, a histogram as shown in FIG. 11 is created (step S431).

From the created histogram in step S431, a density value Th3 indicating the lower limit of the density of a passing-through area is extracted (step S432). Here, the most significant cavity point P of a first recess is defined from the high density value side on the above histogram.

The extracted density value Th3 in step S432 is defined as the first characteristic value S1.

In this manner, in step S412 at the subsequent stage, the appearance frequency at an image end at a certain proportion or more of the first characteristic value S1 (density value Th3) is computed.

Therefore, by using such method, i.e., by computing the first characteristic value S1 from the density value histogram, in the case where a passing-through area is present, the passing-through area density can be computed constantly. As a result, the presence or absence of irradiation collimating can be further judged with higher precision.

(2) Image Enhancement Processing

"Image enhancement processing" is a process for enhancing the frequency of an image.

Methods for image enhancement process of digital X-ray images employed for a medical X-ray photography system include unsharp masking processing well employed in photographic technology or self-compensation filter processing using an analog system filter.

For example, in the unsharp masking processing method, assuming that an image targeted for processing is f (x, y), the resultant image g (x, y) obtained by this process is represented by Equation (3) below.

[Equation 3]

$$g(x, y) = f(x, y) + c \times \{f(x, y) - f_{av}(x, y)\} \quad (3)$$

In the above Equation (3), "fav (x, y)" is a local average value in the coordinate (x, y), and is obtained from the peripheral "n×m" pixel region of the coordinate (x, y). This local average value can also be obtained using a simple average pixel value as shown in Equation (4) below.
[Equation 4]

$$f_{av}(x, y) = \{1/(n \times m)\} \times \Sigma\Sigma f(x-i, y-i) \qquad (4)$$

Such local average value fav (x, y) indicate a blurred image in which a target image f (x, y) is blurred. As the peripheral "n×m" pixel region for obtaining the local average increases, the more blurred image is obtained.

In the above Equation (3), in its second term, the high-frequency component of the target image f (x, y) due to a difference is multiplied by a coefficient "c". That is, in an unsharp masking process, the high-frequency component multiplied by the coefficient "c" is applied to the target image f (x, y).

On the other hand, in the self-filter compensation processing method, the resultant image g' (x, y) obtained by this process is represented by Equation (5) below.
[Equation 5]

$$g'(x, y) = f(x, y) + F\{f_{av}(x, y)\} \qquad (5)$$

In the above Equation (5), as in the above Equation (3), "fav (x, y)" is a local average value in the coordinate (x, y), and indicates a blurred image in which the target image f (x, y) is blurred. In addition, F {*} is a function denoting an analog system filter.

(3) Gradation Conversion Processing

"Gradation conversion processing" is a process for adjusting gradation characteristics (visibility) for a digital X-ray image.

For example, as a general method for a doctor to perform diagnosis using an X-ray image, before outputting the X-ray image to an X-ray film (a silver salt film), the X-ray image is screen-displayed on the display (CRT or the like), and the displayed X-ray image is interactively subjected to gradation processing to convert into an easily diagnostic image, and outputted therefrom to the X-ray film. Therefore, in this method, the doctor undergoes diagnosis by observing an image on the silver salt film.

On the other hand, in recent years, in addition to the above method, there is employed a method (a CRT diagnosis method) for the doctor to diagnose the patient by directly observing the screen-displayed X-ray image on the display without outputting the X-ray image to the silver salt film.

In the meantime, in any of the above methods, it is preferable that an X-ray image screen-displayed on the display is similar to the X-ray film for the doctor in gradation characteristics (visibility). This is because lesions or the like is specifically visualized on the X-ray image by a long designed and sophisticated photography technique, and the doctor has been trained in determining diseases with such visualization mode.

Figure 12:
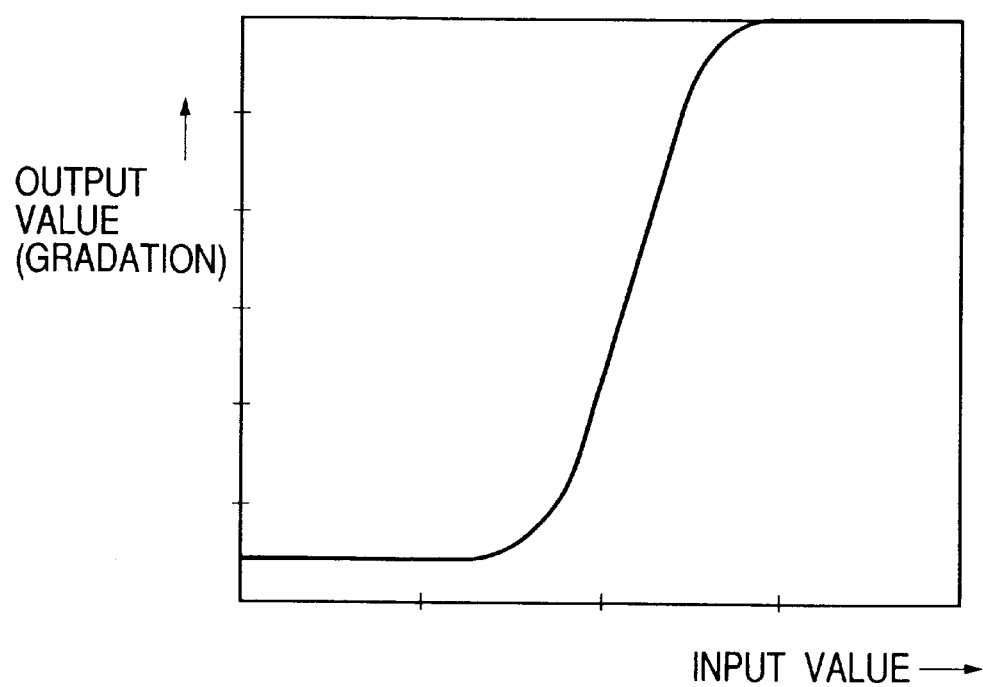
FIG. 12 is a view for illustrating a shape of a general gradation processing function in a gradation conversion process employed as image processing of the above image reading unit.

Therefore, a function frequently used as a function for gradation conversion processing (hereinafter, referred to as "gradation processing function") is S-shaped, as shown in FIG. 12, and a characteristic curve representing X-ray film characteristics is shaped similarly. This function has non-linear characteristics closing to the maximum and minimum values with respect to an input value. There has been proposed a variety of functions (basic gradation processing functions) having such shape.

Therefore, when gradation conversion processing is performed for an X-ray image targeted for processing, using a gradation processing function having a coefficient of the above mentioned basic gradation processing function adjusted, an X-ray image having its gradation characteristics similar to the X-ray film is obtained.

Here, as an example of the gradation conversion processing method, a coefficient of the basic gradation processing function is adjusted to obtain a desired gradation processing function. When gradation conversion processing is performed based on this function, desired maximum and minimum densities are set, and the basic gradation processing function is moved in parallel in accordance with the X-ray image targeted for processing. A method for adjusting the gradation degree of the gradation processing function undergoing this adjustment, thereby to obtain a desired gradation processing function will be described.

The basic gradation processing function D (x) in this gradation conversion processing method is represented by Equation (6) below.

[Equation 6] \hfill (6)

$$D(x) = D_{min} + \frac{D_{max} - D_{min}}{2} \left\{ \frac{1}{1 + \exp(c(x_0 - (x - d)))} + \frac{1}{1 + \exp(a \times c(b \times x_0 - (x - d)))} \right\}$$

In the above Equation (6), "Dmax" and "Dmin" designate a maximum output density value and a minimum density value", "c" designates a gradation degree, "a" and "b" designates constants, and "d" designates a variable for adjusting a parallel movement quantity.

In such Equation (6), when a gradation degree "c" is increased or decreased, an inclination of the basic gradation processing function D (x) increases or decreases. When only a gradation degree "c" is changed, it is characterized that the inclination can be changed with a point (xc, D (xc)) expressed by D (xc)=(Dmax+Dmin)/2 being a center. Further, "xc" at this time is given by the Equation below.

$$xc = \{x0(1+ab)\}/(1+a) + d$$

It is characterized that xc is always close to the maximum density value Dmax and the minimum density value Dmin.

Figure 13A:
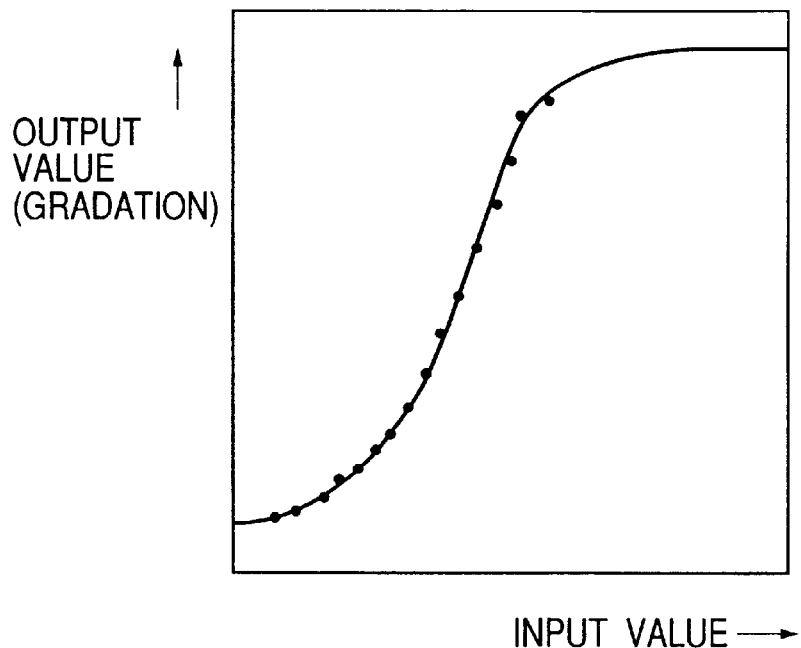
FIG. 13 is comprised of FIGS. 13A and 13B showing views for illustrating approximation of characteristic curves of an X-ray film in the above gradation conversion process.
Figure 13B:
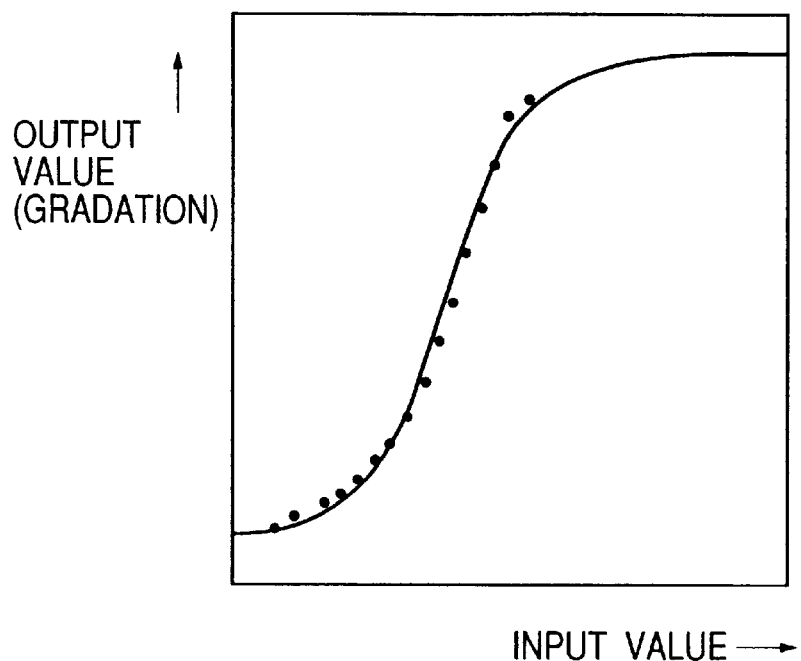

In FIG. 13A, a characteristic curve indicating characteristics of the X-ray film generally employed is approximated by the above Equation (6). This X-ray film characteristic curve can be approximated because there are two terms in { } of the second term of the above Equation (6). Temporarily, when there is only one term in the { }, as shown in FIG. 13B, its difference is evident in comparison with FIG. 13A.

This suggests that the operator easily grasp a concept of gradation conversion processing by providing the operator with approximation of the obtained characteristic curve from the existing X-ray film as described above, as a characteristic curve of the basic gradation processing function D (x) in this gradation conversion processing method.

Constants "a" and "b" in the above Equation (6) are those for expressing a characteristic curve (so-called double gamma characteristics) such that an inclination changes midway in the existing X-ray film. That is, in the above Equation (6), these constants are intended for controlling a gradation degree "c" and "x0" in the second term, as a different inclination is indicated to the first term having the gradation degree "c" and "x0" in { }.

Figure 14A:
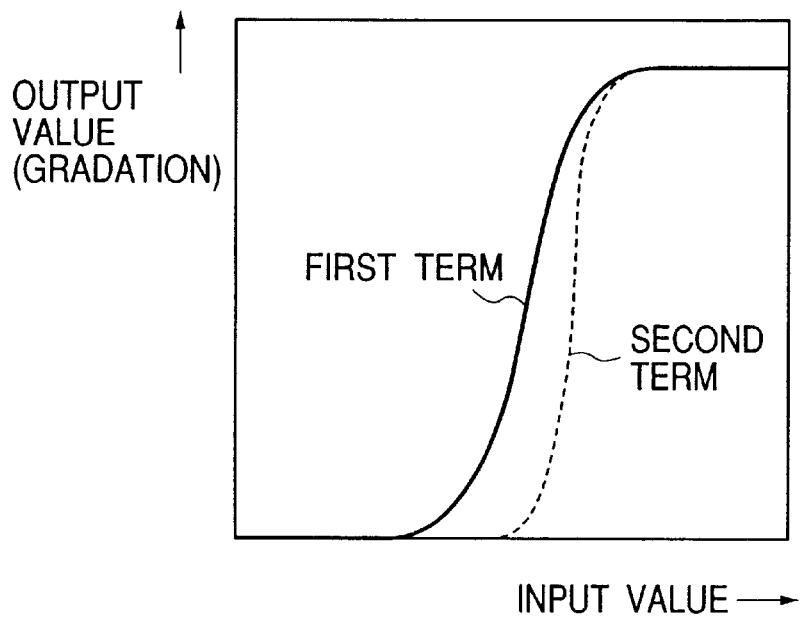
FIG. 14 is comprised of FIGS. 14A and 14B showing views for illustrating a basic gradation processing function in the above gradation conversion process.
Figure 14B:
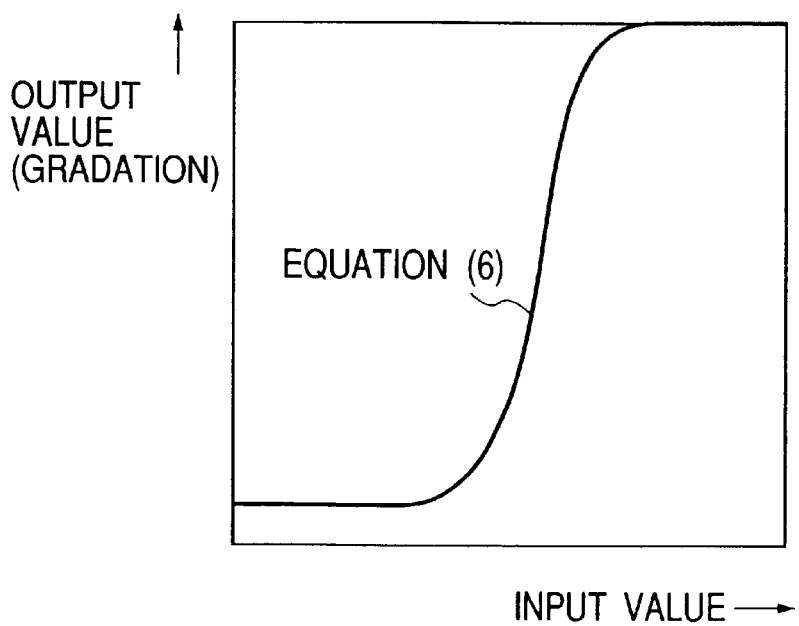

This concept is indicated in FIG. 14A and FIG. 14B. FIG. 14A depicts the first and second terms in { } of the Equation (6); and FIG. 14B depicts a gradation processing function in accordance with the above Equation (6).

As shown in FIG. 14A, with respect to the gradation degree "c" and "x0" in the first term in { } of the above Equation (6), the constants "a" and "b" in the second term have a relationship of "a, b>1".

"b>1" denotes that a second term is present on an input value side higher than a first term; and "a>1" denotes that an inclination is greater than the first term. As a result, there can be formed a gradation processing function having its characteristics in which an inclination is small on the low input value side, and the inclination on the high input value side is greater than on the low input value side.

Thus, in the above Equation (6), the characteristic curve of the existing X-ray film having the complicated characteristic curve can be approximated, which denotes that the characteristic curve of the X-ray film employed in a general facility can be approximated.

When gradation conversion processing as described above is used, image process parameters to be changed and designated by the operator are only variable "d" for adjusting a parallel movement quantity and gradation degree "c".

Figure 15A:
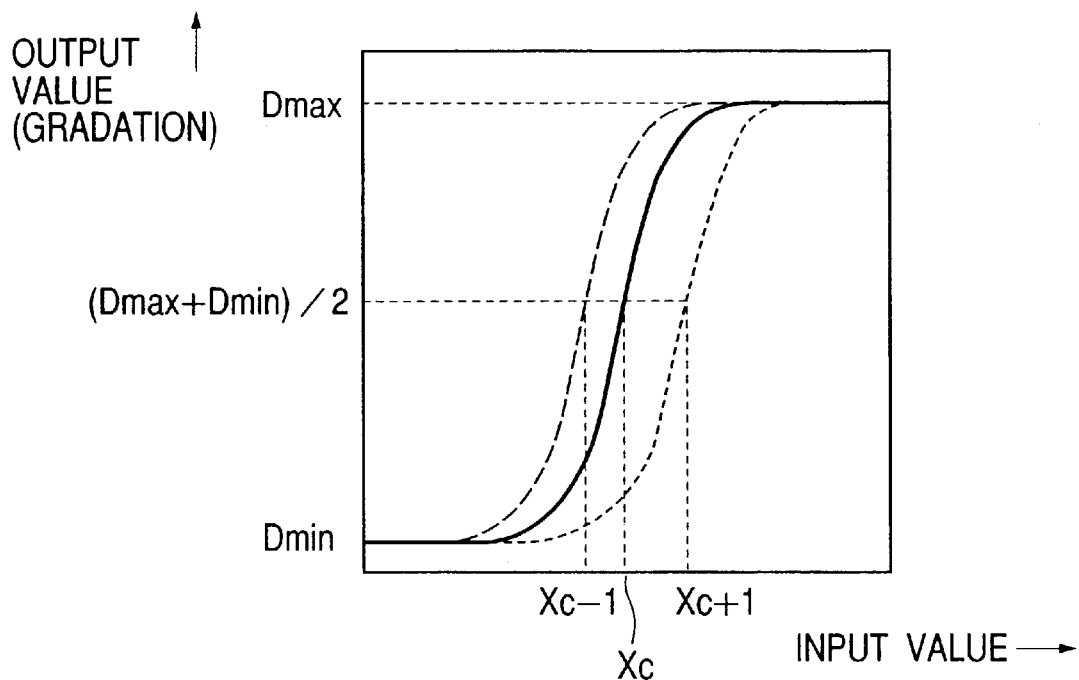
FIG. 15 is comprised of FIGS. 15A and 15B showing views for illustrating parallel movement of the basic gradation processing function and gradation control in the above gradation conversion process.
Figure 15B:
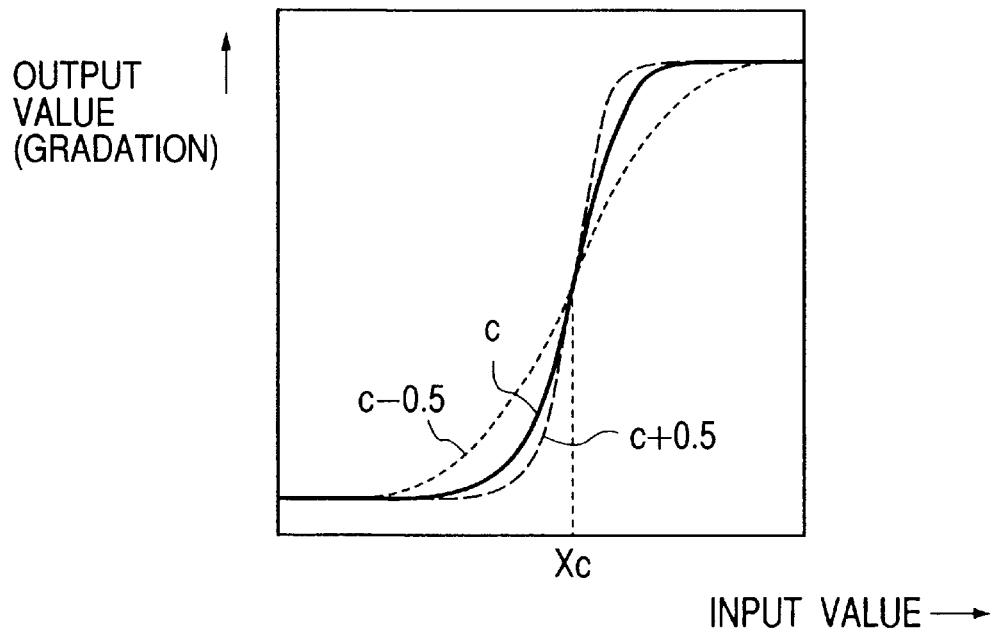

This is because the maximum density Dmax and the minimum density Dmin are generally fixed, "xc" is increased or decreased with adjustment of variable "d", and thus, the operator changes and designates the variable "d" according to input data, thereby causing parallel movement of the basic gradation processing function D (x), as shown in FIG. 15A. That is, it is sufficient that the operator reduces the variable "d" if input data is smaller or increase the variable "d" if the data is greater. In addition, the operator changes and designates the gradation degree "c", thereby, causing the inclination of the basic gradation processing function D (x) to be adjusted, as shown in FIG. 15B. As a result, the contrast of the entire image can be changed.

Figure 16:
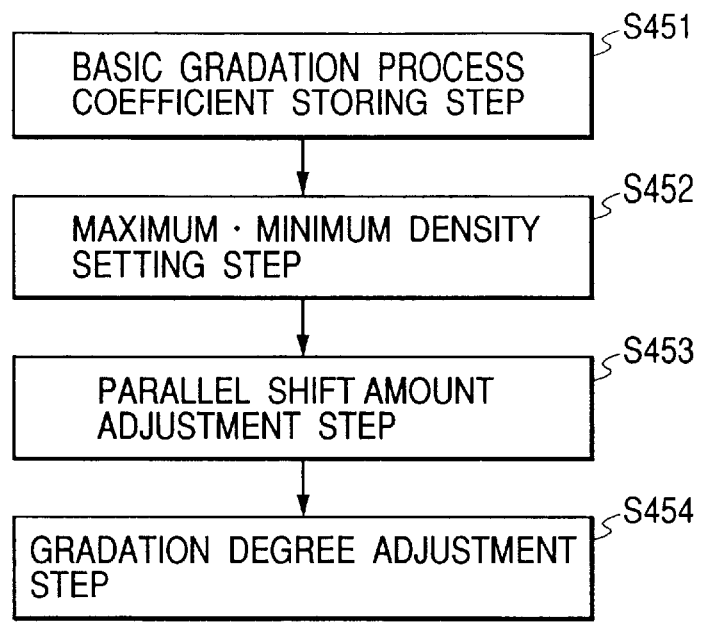
FIG. 16 is a flow chart for illustrating the above gradation conversion process.

FIG. 16 shows this gradation conversion processing by way of showing a flow chart.

First, a coefficient is inputted to the preset basic gradation processing function D (x) (step S451).

In this step S451, gradation conversion processing parameters (image process parameters) may be determined in advance in a "try and error" manner. A characteristic curve of the X-ray film conventionally used by the operator may be employed which is approximated by the above Equation (6). As an approximation method, there is employed a Levenberg-Marquardt method which is generally used as a non-linear minimum square method.

Next, the desired maximum density Dmax and minimum density Dmin are set (step S452).

The maximum density Dmax and the minimum density Dmin are generally fixed, and thus, only standard values may be set.

Then, the basic gradation processing function D (x) suitable to an X-ray image targeted for processing is moved in parallel in accordance with the changed and designated variable "d" (step S453).

When this step S453 is executed, the operator may make adjustment while observing a histogram of the X-ray image targeted for processing.

The X-ray image targeted for processing is processed by employing the adjusted basic gradation processing function D (x) in steps S451 to S452, thereby to obtain the X-ray image having desired contrast (step S454).

As described above, in this gradation conversion processing, image process parameters frequently changed and designated by the operator are variable "d" for adjusting a parallel movement quantity and a gradation degree "c". Mere adjustment may be made such that any variable is increased or decreased from the initial setting of the basic gradation processing function. Therefore, this gradation conversion processing is used, thereby making it possible to use an input/output device with its simplicity and high operability such as vertical or horizontal mouse operation as a device for changing or designating image process parameters.

In addition, the magnet (6) is used, thereby making it possible to express a characteristic curve indicating the existing X-ray film characteristics, and thus, the meaning of the basic gradation processing function for operator's adjustment is made clear.

In the above mentioned gradation conversion processing method, the variable "d" to be changed or designated by the operator may be automatically set by analyzing an X-ray image targeted for processing.

Figure 17:
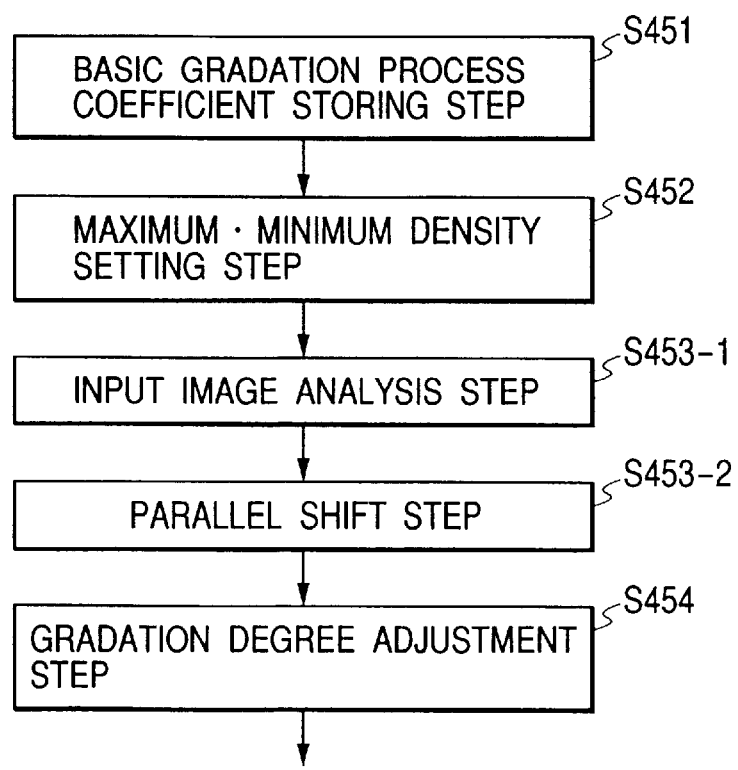
FIG. 17 is a flow chart for illustrating a case when the step of performing input image analysis is added in the above gradation conversion process.

In this case, this gradation conversion processing is shown in a flow chart as shown in FIG. 17.

That is, as described above, a coefficient is inputted to the preset basic gradation processing function D (x), and the desired maximum density Dmax and minimum density Dmin are set (steps S451 and S452).

Next, the variable "d" is computed by analyzing an X-ray image targeted for processing (step S453-1). To analyze the X-ray image, there is employed a method for employing a center value of a histogram in an effective region (such as the above mentioned irradiation field area) of the X-ray image targeted for processing or its gravity.

Then, based on the variable "d" computed in step S453-1, parallel movement of the basic gradation processing function D (x) is performed (step S453-2).

The adjusted basic gradation processing function D (x) in steps S451 to S452 is used to process an X-ray image targeted for processing, thereby obtaining an X-ray image having its desired contrast (step S454).

Therefore, the operator may adjust only a gradation degree "c" by using such method, thus making it possible to change or designate simple and fast image process parameters.

In addition, each image process parameter may be set so that an input value of the basic gradation processing function D (x) is fixed to an X-ray irradiation quantity, for example.

In this case, variables such as variable "d" or gradation degree "c" are computed from image collection conditions such as X-ray irradiation quantity, and the computation results are stored in a memory or the like corresponding to the image collection conditions.

Therefore, using such method makes it possible to momentarily judge whether or not photographing conditions are proper. Even if the photographing conditions are not proper, gradation conversion processing results having good contrast can be obtained by making re-adjustment. The excess or shortage of X-ray irradiation quantity can be directly judged as in a conventional X-ray film.

A description of (1) irradiation field recognition processing; (2) image enhancement processing; and (3) gradation conversion processing has now been completed.

Hereinafter, determination of image process parameters at the image read control unit 122 of FIG. 1 for executing image processing using each of processes (1) to (3) will be described.

As described above, (1) irradiation field recognition processing; (2) image enhancement processing; and (3) gradation conversion processing each are executed in order.

Here, all of these processes are executed in 4096 gradation gray scale, and image data (reduced natural image data) obtained after execution of processing is written into an area (RAM 124 or the like) for representing 8-bit data of horizontal 336 pixels and vertical 336 pixels, and is screen-displayed at the overview display port 304 of the display 132 via the user IF unit 129. In addition, at this time, the user IF unit 129 holds a table for correcting gamma on the screen of the display 132 in advance. In this manner, the linearity on the screen of the display 132 is placed in a corrected state.

FIG. 18 shows details on image process parameters in each of processes (1) to (3).

As shown in FIG. 18, default values of image process parameters are preset to each of processes (1) to (3) according to each region of interest.

Using such default values, the image read control unit 122 executes the above mentioned operation process task 321 (refer to FIG. 4), and thus image parameters are determined as follows:

First, with respect to (1) determination of image process parameters for irradiation field recognition processing, when "Auto" is set, parameters for a reduced natural image (width, height, and extraction start position of an extraction area) are automatically determined using the preset default values. Therefore, an irradiation field area is recognized (extracted) for reduced natural image data using the automatically determined parameters.

As described above, reduced natural image data is reduced to 1/8 of natural image data in size. When this processing is performed for natural image data, automatically determined parameters are multiplied by 8 times for reduced natural image data.

On the other hand, when "Designated" is set, the operator performs an operation for clicking two parts, i.e., the upper left and lower right of the irradiation field area in a reduced image displayed on the screen of the display 132 by using mouse of the operating unit 133 or the like, and designates the irradiation field area. Alternatively, the operator designates an arbitrary area (that is, a predetermined area is specified without recognizing the irradiation field area).

In this case, the default values (width W, height H, and extraction start positions X and Y of the extraction area) for parameters in accordance with this specification are reduced to 1/8 times, the reduced values are used as parameters for reduced natural image data, and the irradiation field area is recognized for the reduced natural image data.

In this case, similarly, when this processing is performed for natural image data, parameters determined for reduced natural image data are multiplied by 8 times.

Next, with respect to determination of image parameter parameters for image enhancement processing, four stages of 0 (general), 10 (weak), 20 (middle), and 30 (strong) can be set. With respect to these settings, the value to be set in experience as parameters for natural image data are preset as a default value (N).

Here, when this processing is performed using the preset default value (N) for reduced natural image data as is, it is likely to be visually enhanced too much in comparison with when similar processing using the same parameter value (N) is done for natural image data. To prevent this, the parameter value (N) may be reduced to 1/8 because the size ratio of reduced natural image data to natural image data is 1/8 time; and however, it is possible to visualize whether or not image enhancement processing is done.

As parameters for reduced natural image data, the default value N is reduced to 1/2 time. Using such parameters, when this processing is performed for reduced natural image data, the visibility of the reduced image data is substantially similar to natural image data after the processing.

When image enhancement processing is performed for natural image data, parameters determined for reduced natural image data is doubled.

For image enhancement processing, the operator can change parameters by clicking by the mouse of the operating unit 133 an image process change instruction buttons 305 (refer to FIG. 2, "S+" and S−" buttons) on the display screen of the display 132. In this case also, similarly, when the parameters determined by the operator are employed for natural image data, a value twice as large as the data is used.

Next, for determination of image process parameters for gradation conversion processing, parameters for reduced natural image data are automatically determined using an area (an irradiation field area) for results obtained by irradiation field recognition processing.

When image enhancement processing is performed for natural image data, the same parameter as those automatically determined for reduced natural image data are used.

As described above, the image read control unit 122 determines image process parameters for each process using default values by the preset region in accordance with rules shown in FIG. 18 for reduced natural image data. The control unit 122 does not determine all image process parameters by simply reducing the default values to 1/8 (reduction ratio).

An image of obtained results by image processes of (1) to (3) as described above is screen-displayed at the overview display port 304 of the display 132. The operator clicks a processing OK button 307 provided on the display screen by means of the mouse of the operating unit 133 when the operator observes a screen-displayed image, and judges the image to be proper (refer to FIG. 2).

In this manner, image processing at this time is defined (determined), and image process parameters during the determined image processing are stored in a nonvolatile storing unit 128 corresponding to the already stored natural image data.

The operator selects the corresponding region setting button 306 for the region of interest as described above for the next photography. Alternatively, when photography is ended (when examination is ended for patients at this time), the operator selects an inspection end 308.

Through any operation, the image read control unit 122 performs non-reversible compression using a non-reversible compression coefficient predefined by region for reduced natural image data (display data) consisting of 8-bit data of the above mentioned horizontal 336 pixels and vertical 336 pixels. In addition, the image read control unit 122 computes the compression rate based on a ratio between byte size of an original image and byte size of a non-reversible compressed image. The thus obtained compression ratio is held together with an image attribution described later, and is used for processing at the next stage.

The non-reversible compression coefficient used for the above non-reversible compression is required to be different from each other every region because, for example, relatively high-precision images are required in diagnosis using a breast image, and even if high compression is performed, it is required to hold a sufficient image for diagnosis in bone-image diagnosis in orthopedic surgery.

As described above, the operator can perform a plurality of photographing processes sequentially by changing a region of interest for one object 200 (one patient). However, before selecting the inspection end 308 for ending all photographing processes, it is required to input information concerning the object 200 (information such as patient name by operation of the above mentioned input button 302).

At this time, when the operator has selected the inspection end 308 without performing the input operation, for example, an additional information input window (a patient information input window) automatically opens on the display screen of the display 132 at a timing when the inspection end 308 has been selected, and information can be inputted from the window. When information concerning the object 200 is inputted by the operator, and the completion of input is instructed, the photography is automatically ended. A series of obtained images during this photography (the obtained image at the image read control unit 122) are formed so as to be inputted to an image process queue part 326 as a queue (refer to FIG. 4).

[Overview Display at the Display 132]

An overview display port 304 is provided on the display screen of the display 132 as shown in FIG. 2.

The operator selects a desired image of X-ray images (reduced natural images) displayed in array using the mouse of the operating unit 133, thereby making it possible to cause the image to be re-displayed at the image display 301.

Figure 19:
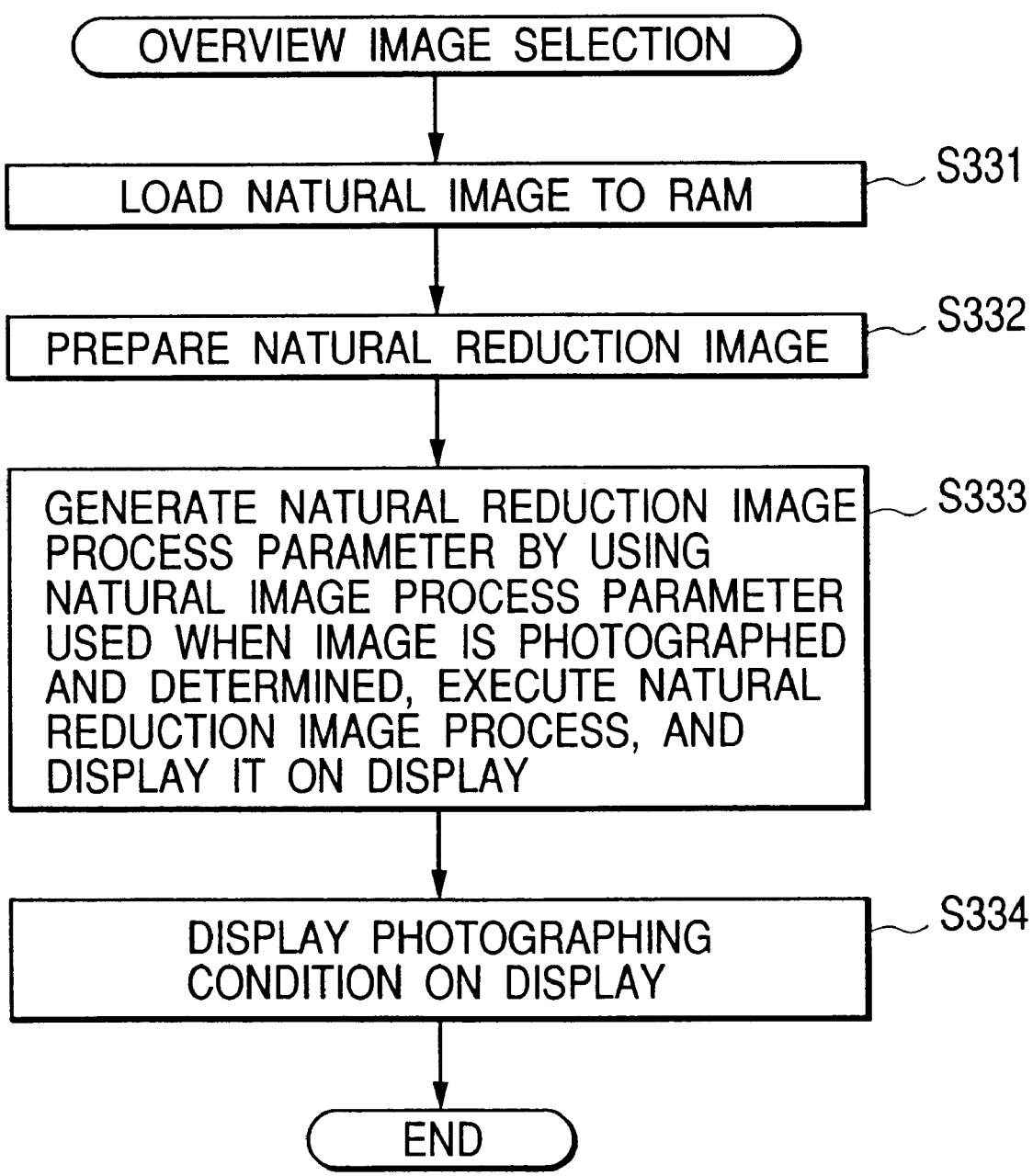
FIG. 19 is a flow chart for illustrating overview display at the above display.

Such operation is achieved by processing in accordance with a flow chart shown in FIG. 19, which is performed at the image read control unit 122 shown in FIG. 5.

From a nonvolatile storing unit 128, natural image data corresponding to a selected image at the overview display port 304 is read out, and the natural image data is loaded on a RAM 124 (step S331).

Next, reduced natural image data is produced from the loaded natural image data on the RAM 124 (step S332).

Then, during photography of the selected image at the overview display port 304, image process parameters for the determined natural image data as described above are assumed as default values as shown in FIG. 18, and image process parameters for reduced natural image data is produced in accordance with rules shown in the figure. Using the produced, reduced image process parameters, image processing is performed for reduced natural image data, and the image is displayed on the image display port 301 of the display 132 (step S333).

Simultaneously, photographing conditions at that time (natural image process parameters according to parameters for reduction image process) are re-displayed at the photography condition display port 303 of the display 132 (step 334).

In the above mentioned operation, after the already stored natural image data in the nonvolatile storing unit 128 has been allocated again on the RAM 124, when the operator operates the region setting button 306 again, the already photographed and obtained X-ray image can be handled as an X-ray image photographed in a different region.

That is, even if the operator selects a different region setting button 306 incorrectly, thereby photography operation is advanced, and image collection is performed, and then, the region setting button 306 is operated as a different region, setting of the information of various attributions and image processing are redone, and are changed in a different region.

Such operation during re-selection with the region setting button 306 is achieved by processing in accordance with a flow chart shown in FIG. 20, for example.

First, the image read control unit 122 displays the fact that "region change" is made (warning panel message) on the display screen of the display 132 when it recognizes that the region setting button 306 is operated after the X-ray image has been screen-displayed on the display 132 via a user IF unit 129. In this manner, the operator select an OK button (not shown) on the display screen of the display 132 by using the mouse of the operating unit 133 (step S341).

Next, the image read control unit 122 generates image process parameters for reduced natural image data using the default values for image process parameters as shown in FIG. 18, i.e., using the preset default values for a re-selected region. Using the default value, the control unit 122 performs image processing for the reduced natural image data. The image read control unit 122 re-displays an image undergoing the image processing on the image display port 301 of the display 132 via the user IF unit 129 (step S342).

Further, the image read control unit 122 re-displays photographing conditions on the photographing condition display port 303 of the display 132 via the user IF unit 129 (step S343).

In step S333 of the FIG. 19 and step S342 of FIG. 20, as described above, of course, the operator can re-change image process parameters.

[Format of a Photography Information File Generated after the End of Photography]

To end one or a plurality of photography processes (i.e., to end examination for one patient), as described above, the operator may select the inspection end 308 on the display screen of the display 132 by using the mouse of the operating unit 133. At this time, as shown in FIG. 4, a process after the end of photography at the apparatus is executed on background by all multi-task processes. In this manner, the operator can move to the next photography again immediately.

FIG. 21 shows a format of a photography information file (an examination file) generated at the end of photography.

For example, the image read control unit 122 generates one examination file in accordance with a format of FIG. 21 when it recognizes that the inspection end 308 has been operated on the display screen of the display 132 via the user IF unit 129.

The examination file created here contains one examination attribution and a plurality of image attributions as shown in FIG. 21.

The examination attribution contains a patient attributions, an examination specific attribution, and the number of photographed images. The patient attribution contains patient ID, patient name, date of birth, and gender or the like. The examination specific attribution contains information such as examination ID, date of examination, and examination time or the like. The number of photographed images indicates the total number of image attributions written in this examination file.

The image attribution contains region name, photographing conditions, natural image processing conditions, non-reversible compression ratio, and natural image file name.

Region name indicates the name of region in which photography has been performed. Photographing conditions indicate tube voltage, tube current or the like. Natural image processing conditions indicate image process parameters for natural image data as shown in FIG. 18. Non-reversible compression coefficient and non-reversible compression ratio indicate a compression coefficient employed for non-reversible compression when the above mentioned image processing is determined, and a compression ratio computed and obtained at that time. Natural image file name indicates a file name when natural image data is stored in the nonvolatile storing unit 128 as described above.

As described above, an examination file contains the examination information and all information of the nonvolatile storing unit 128 to be linked with a file. When this examination file name is managed by a non-volatile queue, an apparatus in this embodiment is constructed.

[Management of Queue Units 326, 327, and 328]

As shown in FIG. 4, processes such as image processing, image transmission, and image deletion are performed on background. In this duration, data is exchanged by an image process queue part 326, an image sending queue part 327, and an image erase queue part 328.

Here, it is characterized that these image processing queue 326, image sending queue parts 327, and image erase queue part 328 are managed in one table. Hereinafter, this table is referred to as "a queue table".

FIG. 22 shows a configuration of the above queue table. In FIG. 22, there is shown that, when one examination in which photography of the object 200 (patient) is composed of a plurality of X-ray images is stored in the nonvolatile storing unit 128 as an examination file, and is inputted to an image process queue part 326, a new QID is issued on the queue table, and one line is added to the bottom line.

This queue table will be described in detail.

The queue table as described above is stored in a nonvolatile storing unit 128 so that a plurality of back process tasks 322 to 325 and only one operation process task 321 performs rewriting. Thus, exclusive processing called semaphore processing is performed, and it is required for another task not to perform writing into the queue table.

Therefore, each task is achieved so as to provide access to the queue table as follows:

In the foregoing description, obtaining privilege for writing into the queue table is called "obtain queue semaphore", and stopping privilege for such writing is called "release queue semaphore".

Figure 23:
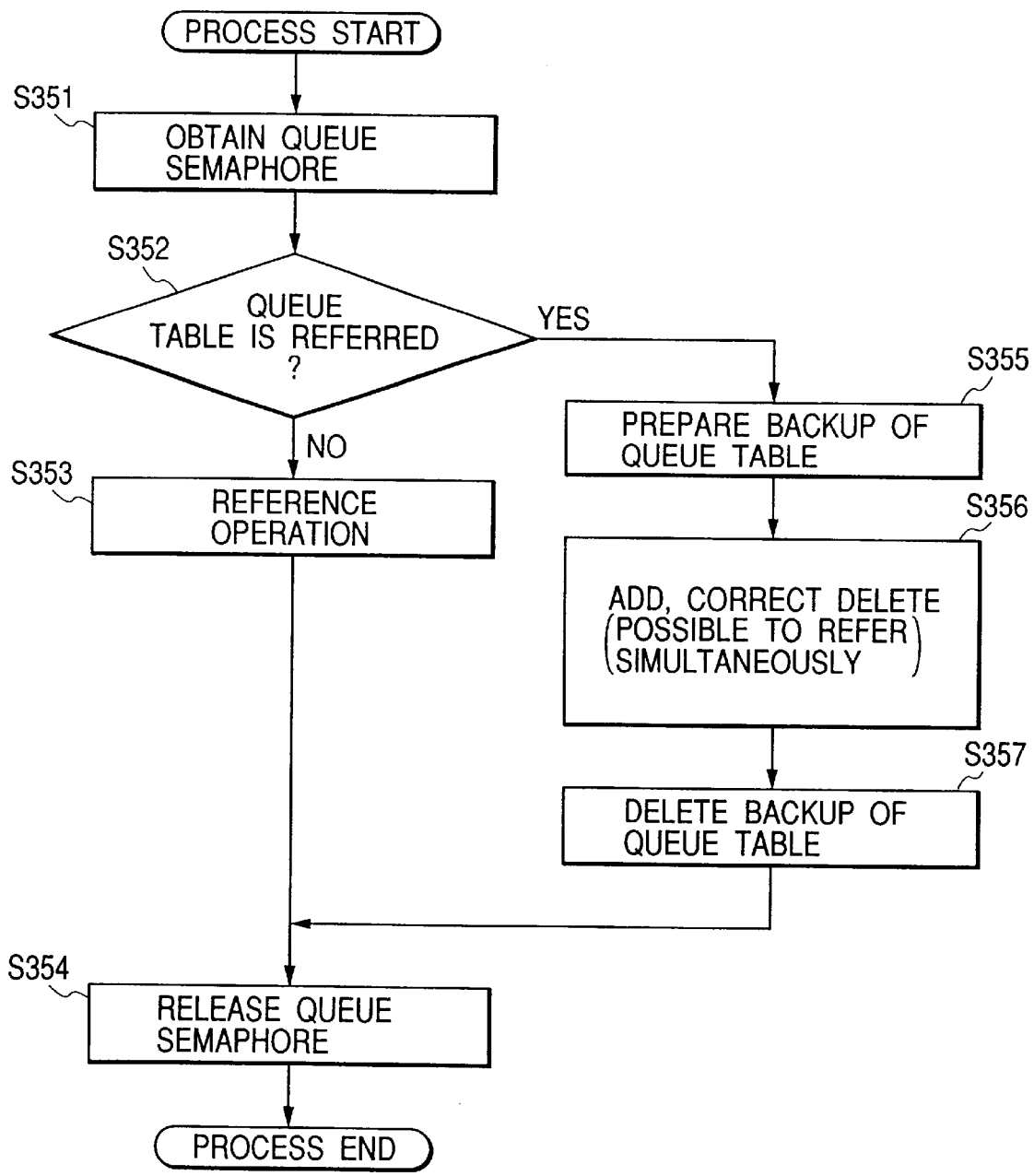
FIG. 23 is a flow chart for illustrating reference, addition, correction, and deletion for the above queue table.

FIG. 23 shows processes (jobs) for referencing, adding, correcting, and erasing a processing status of an examination file for the queue table in each task.

First, a queue semaphore is obtained (step S351).

When a queue table is referenced (step S352), the reference job is performed (step S353). Then, the queue semaphore is released (step S354).

On the other hand, when a queue table is added, corrected, and erased (step S352), a backup table of the queue table is generated by copying the queue table (step S355), and addition, correction, and deletion jobs for a search file are performed (step S356). In these jobs, two or more of the addition, correction, and deletion jobs can be performed in all, and further, the reference job can be performed. Then, the backup table of the queue table is erased (step S357), and the queue semaphore is released (step S354).

As described above, for addition of an examination file to a queue table, a queue semaphore is obtained, the examination file is added to the newly issued QID below the bottom line on the queue table, and then, the queue semaphore is released.

Now, the queue table shown in FIG. 22 will be specifically described. For clarity, terms "Undone", "Running" and "Done" are substituted for its processing statues. However, actually, each of the values "−1", "−2", and "−3" or the like is used.

Each of the columns "Image processing", "Transfer 1" to "Transfer 4", and "Erase" indicates processing that must be performed on background.

The column "Image processing" indicates an execution state of image processing using image process parameters for natural image data as described above.

Each of the columns "Transfer 1" to "Transfer 4" indicates an execution state of processing for transferring to an external device the natural image data undergoing the above image processing. The external device is a server device connected to network, a printer device, or an external portable media recording device directly connected via SCSI or the like.

The column "Erase" indicates processing for erasing image data regarding a queue table having natural image data undergoing all the above transfers or natural image data after image processing or the like stored in the nonvolatile storing unit 128 (hard disk).

Each line of the queue table is called "queue", here.

In the queue table of FIG. 22, when an examination file is inputted to the image process queue part 326, "Undone" which indicates that processing is not done regarding each of the columns "Image processing", "Transfer 1" to "Transfer 4", and "Erase" of the thus generated new QID=2334 is described. "Undone" indicates that any of back process tasks 322 to 325 does not perform a job indicated by that column.

On the other hand, in QID=2329, regarding the column "Transfer 4", the columns "Running" and "TID=1" are described. The column "Running" indicates that one back process task is executing a job indicated by that column. "TID=1" indicates ID of the task performing the job. This indication applies to QID=2330.

In QID=2329, "Done" is described regarding each of the columns "Image processing", and "Transfer 1" to "Transfer 3". The "Done" indicates that a job indicated by that column is ended.

Figure 24B:
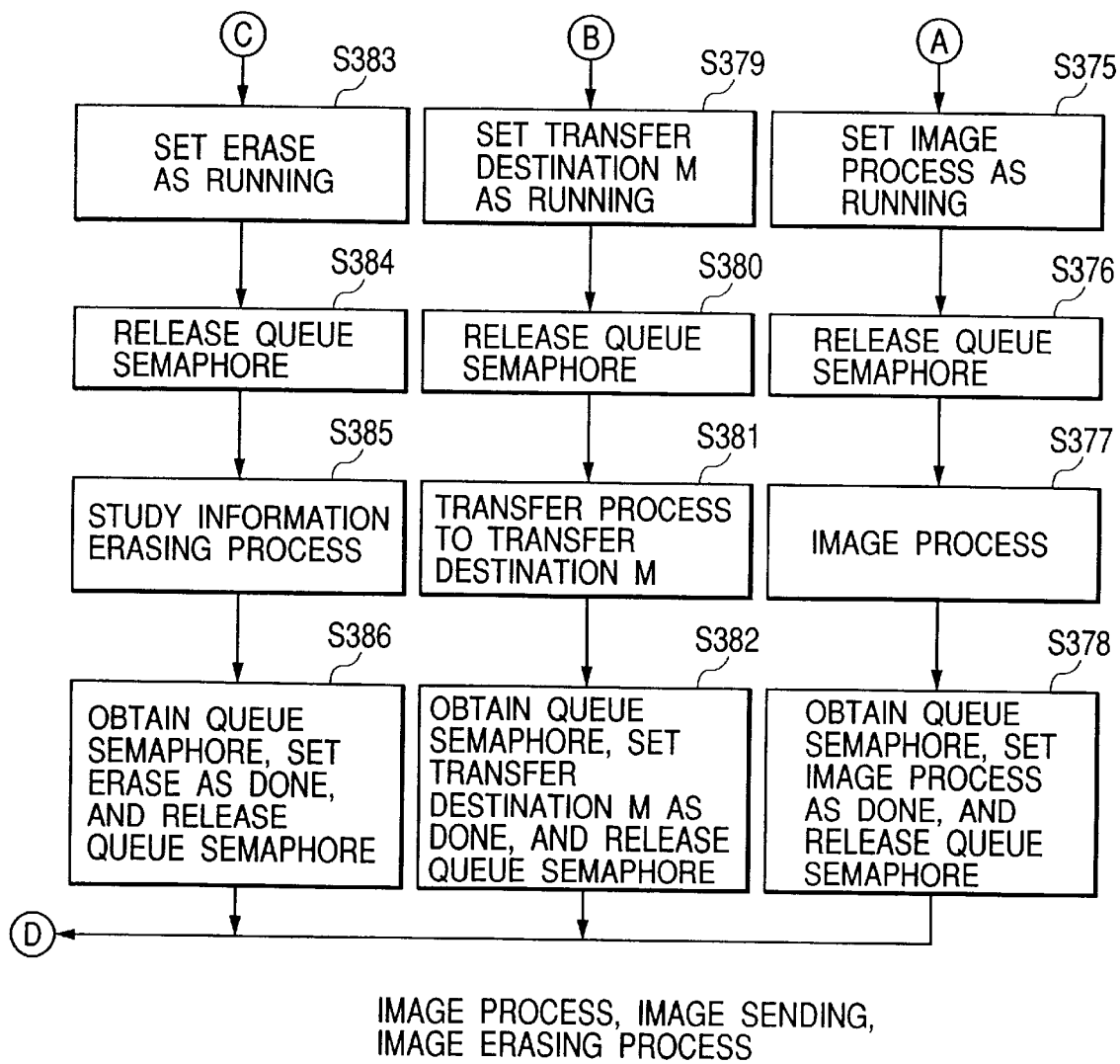
FIG. 24 is comprised of FIGS. 24A and 24B showing views for illustrating a process (1) at a task for accessing the above queue table.

FIGS. 24A and 24B show flows of processing executed by back process tasks 322 to 325 while referring to the queue table described with the above "Undone", "Running", Each of these back process tasks 322 to 325 advances processing as follows by the same control method as shown in FIGS. 24A and 24B.

First, when one back process task starts execution of processing, it is required to refer to a queue table, and therefore, a queue semaphore is obtained(step S361). At this time, if a queue semaphore cannot be obtained, control of the back process task does not advance at that time, and a waiting state is entered until another third person task releases the queue semaphore.

Next, a counter N for starting reading of the N-th queue from the head of the queue table is initially set to "1" (step S362).

Then, the N-th information is read from the first queue (step S363).

Then, it is discriminated whether or not the N-th queue exists (step S364). If no queue exists, a queue semaphore is released (step S374), and processing returns to the first step S361.

On the other hand, if N-th queue exists during discrimination in step S364, the contents of the column regarding "Image processing" is checked (step S365).

As a result of checking in step S365, when the result is "undone", processing" in the N-th queue is set to "Running", and the task ID of the self task is set (step S375).

Next, a queue semaphore is released (step S376).

Figure 25:
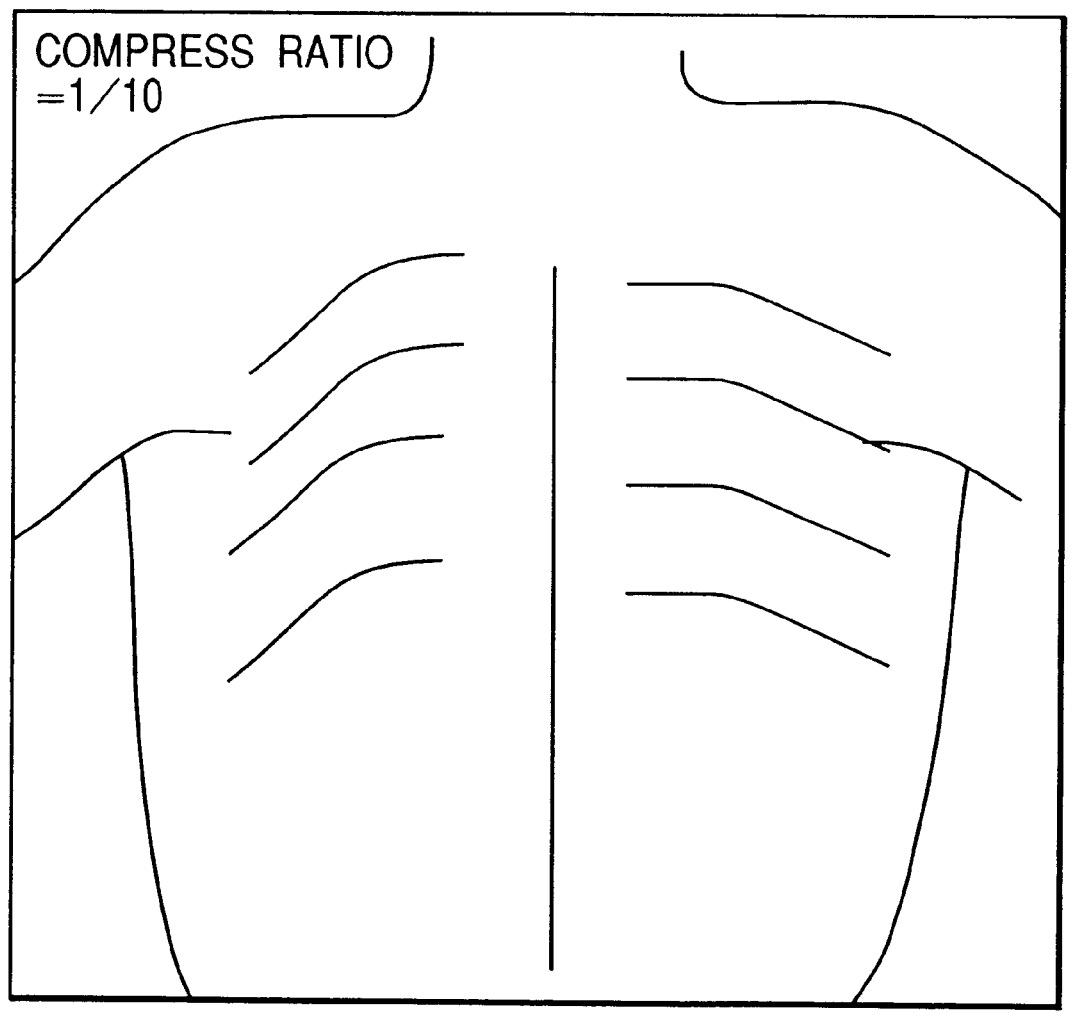
FIG. 25 is a view for illustrating bit map embedding of non-reversible compressing ratio in the above task processing.

Then, an examination file described in the N-th queue, and image processing is performed for natural image data indicated in this examination file (step S377). It is characterized that the image processing is performed using image process parameters for natural image data as described above; and the non-reversible compression rate indicated by "Image Attribution" of the examination file is embedded as a bit map on natural image data, as shown in FIG. 25, for example, and up to non-reversible compression is performed. That is, the image processing designates up to image compression process.

Next, a queue semaphore is obtained again, the column "Running" is set to "Done", semaphore is released (step S378).

Then, processing returns to the first step S361.

Thus, while image processing is actually performed, a queue semaphore is released; and therefore, a back process task other than that undergoing the image processing or an operation process task can obtain a queue semaphore when it performs any job. This is the most significant point.

In addition, as a result of checking in step S365, when the result is "Running", the counter N is counted up by 1 to go to the next queue (step S373), and processing returns to the step S363.

In addition, as a result of checking in step S365, when the result is "Done", set to "1" to perform transfer processing indicated by the columns "Transfer 1" to "Transfer 4" (step S366).

Then, the contents of the column (column "Transfer M") indicated by the counter M are checked (step S367).

As a result of checking in step S367, when the result is "undone", the column "Transfer M" in the N-th queue is set to "Running", and the task ID of the self task is set (step S379).

Next, a queue semaphore is released (step S375).

Then, an examination file described in the N-th queue, transfer processing indicated by the column "Transfer M" is performed for natural image data indicated in this examination file (step S381). The transfer processing at this time is a job for transferring data to a predetermined transfer destination in the apparatus.

Then, a queue semaphore is obtained again, the column "Running" is set to "Done", and the queue semaphore is released (step S382).

Then, processing returns to the first step S361.

Thus, while transfer processing is actually performed, a queue semaphore is released; and therefore, a back process task other than that undergoing the transfer processing or an operation process task can obtain a queue semaphore when any job is performed. This is the most significant point.

In addition, as a result of checking in step S367, when the result is "Running" or "Done", the counter M is counted up by "1" (step S368).

Next, it is discriminated whether or not the value of the counter value M exceeds "4" (step S369). As a result of this discrimination, if the above value does not exceed 4, processing returns to step S367. In this manner, processing for all "Transfer 1" to "Transfer 4" is performed.

If the value of the counter M exceeds "4", it is discriminated whether or not each of the columns "Transfer 1" to "Transfer 4" is set to "Done" (step S370).

As a result of discrimination in step S370, when all of the results are not "Done", the counter N is counted up by "1", and processing returns to step S373. This indicates that, if one "Running" exists in each of the column "Transfer 1" to "Transfer 4", processing can move to execution of processing for the next queue.

On the other hand, as a result of discrimination in step S370, when all of the results are "Done", the contents of the column of "Erase" are checked (step S371).

As a result of checking in step S371, when the result is "Undone", the column "Erase" in the N-th queue is set to "Running", and the task ID of the self task is set (step S383).

Next, a queue semaphore is released (step S384).

Then, the examination file described in the N-th queue is read, and erase processing is performed for natural image data indicated in this examination file (step S385). The erase processing at this time indicates erasing an examination file stored in the nonvolatile storing unit 128, a plurality of sets of natural image data designated by the contents of the examination file, and natural image data which is a result of image processing done for the natural image data.

Then, a queue semaphore is obtained, the column "Running" is set to "Done", and the queue semaphore is released (step S386).

Then, processing returns to the first step S361.

Thus, while erase processing is actually performed, the queue semaphore is released; and therefore, a back process task other than that undergoing the erase processing or an operation process task can obtain a queue semaphore when any job is performed. This is the most significant point.

In addition, as a result of checking in step S371, when the result is "Running", the counter N is counted up by "1" (step S373), and processing returns to step S363.

Further, as a result of checking in step S371, when the result is "Done", the N-th queue is erased from the queue table (step S372). In this manner, the least significant queue than the N-th queue sequentially moves upwardly.

Then, the queue semaphore is released (step S374), and processing returns to the first step S362.

By following the flow of processing as shown in FIGS. 24A and 24B, a plurality of back process tasks 322 to 325 are synchronized with each other, and processing for the queue table can be advanced.

Figure 26B:
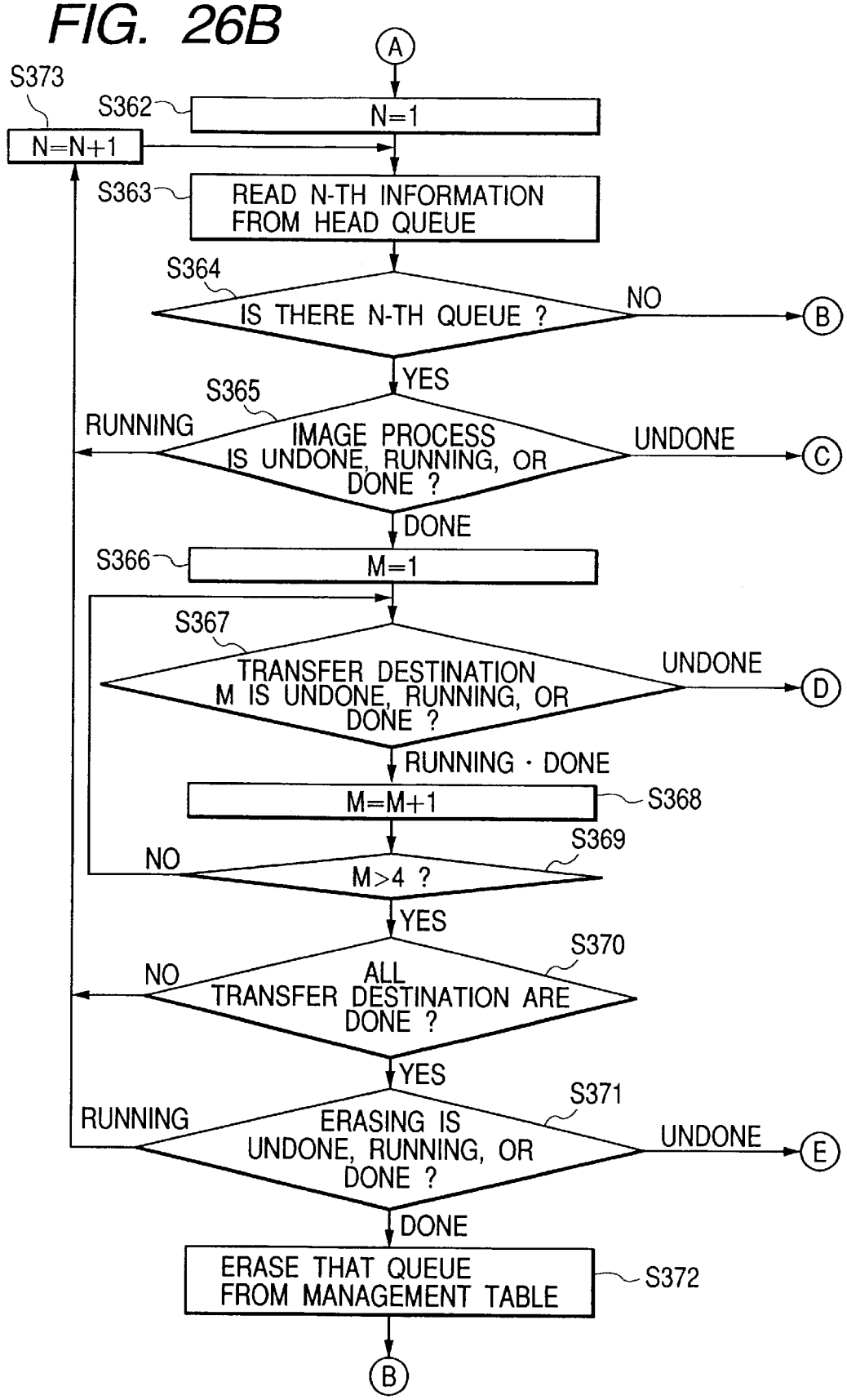
FIG. 26 is comprised of FIGS. 26A, 26B and 26C showing views for illustrating a process (2) at a task for accessing the above queue table.
Figure 26C:
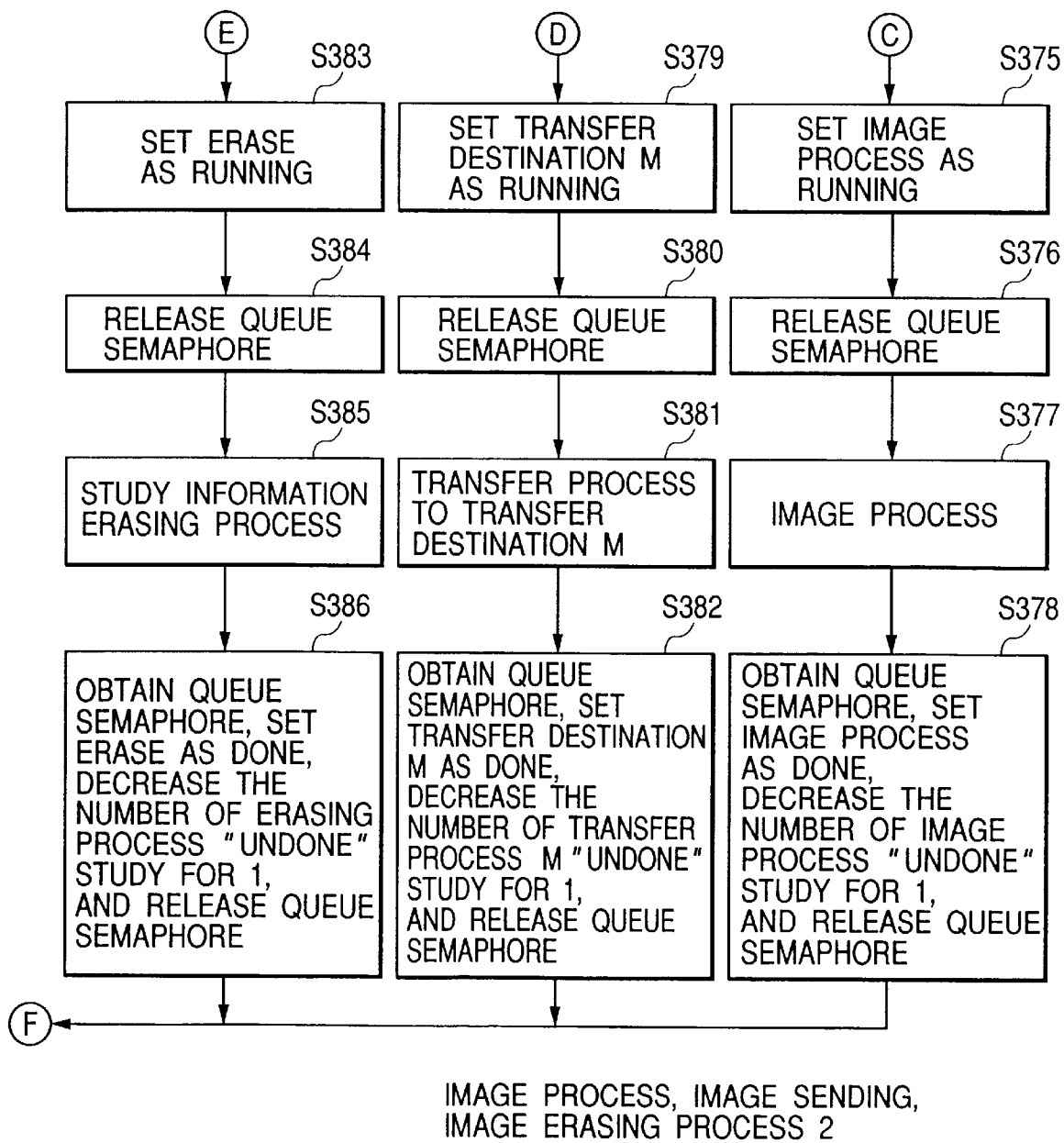

The flow of processing shown in FIGS. 24A and 24B may be as shown in FIGS. 26A to 26C.

That is, in FIG. 26, before the back process tasks 322 to 325 provide access to the queue table stored in the nonvolatile storing unit 128, consideration is taken so as to store whether or not it is necessary to provide such access on the RAM 124, thereby aiming to improve the processing speed.

In the flow chart in FIGS. 26A to 26C, the steps for performing processing in the same way as the flow chart in FIGS. 24A and 24B are designated by the same reference numerals, a detailed description of which is omitted here.

Specifically, a difference from the flow of processing in FIGS. 24A and 24B are that processing in steps S391 to 396 is added between obtaining a queue semaphore in step S361 and initial setting of the counter N in step S362.

When the flow of such processing is executed, in the case where a queue is added to the queue table, it is assumed that variables indicating the number of studies (the number of studies indicated by "Undone" in the columns "Image processing", "Transfer 1", "Transfer 2", "Transfer 3", "Transfer 4", "Erase") is increased by "1".

As described above, a queue semaphore is obtained (step S361).

Then, it is discriminated whether or not the number of studies indicated by "Undone" in the column "Image processing" is "1" or more (step S391).

As a result of this discrimination, when the result is "1" or more, it means that at least one queue requiring image processing exists; and therefore, it goes to the processing from the above mentioned step S362.

On the other hand, as a result of discrimination in step S391, when the result is not "1" or more, i.e., when the result is "0", the counter P is initially set to "1" to check the number of studies indicated by "undone" in the column "Transfer 1" to "Transfer 4" (step S392).

Next, it is discriminated whether or not the number of studies indicated by "Undone" in the column "Transfer P" indicated by the counter P is "1" or more (step S393).

As a result of the discrimination of step S393, when the result is "1" or more, it means that at least one queue requiring transfer processing exists; and therefore, it goes to processing from the above mentioned step S362.

Further, as a result of the discrimination in step S393, when the result is not "1" or less, the counter P is counted up by "1" (step S394), and it is discriminated whether or not the value of the counter P exceeds "4" (step S395). As a result of this discrimination, if the result does not exceed 4, processing returns to step S393. In this manner, processing for all of "Transfer 1" to "Transfer 4" is performed.

If the value of the counter P exceeds "4", it is discriminated whether or not the number of studies indicated by "Undone" in the column "Erase" is "1" or more (step S396).

As a result of the discrimination in step S396, when the result is "1" or more, it means that at least one queue requiring erase processing exists; and therefore, it goes to processing from the above mentioned step S362.

In addition, as a result of the discrimination in step S396, when the result is not "1" or more, the queue semaphore is released (step S374), and processing returns to the first step S361.

As described above, in the flow of processing in FIGS. 26A to 26C, when the number of studies indicated by "Undone" in each of the columns "Image processing", "Transfer 1" to "Transfer 4", and "Erase" is "1" or more, all processing goes to step S362, and subsequently, everything is done in accordance with processing similar to that in FIGS. 24A and 24B.

However, although not shown, the step of reducing the number of studies indicated by "Undone" by "1" is added after each process has been ended.

In addition, since the queue table as described above is stored in the nonvolatile storing unit 128, in the case where the operators turns OFF the power of the apparatus intentionally or accidentally or the like, although a inactive task exists, the result may be "Running" on the queue table at the next initiation.

Therefore, for the purpose of getting ready for such a case, if a backup table of a queue table exists when power is turned ON, the queue table is erased, the backup table is defined as a new queue table, and further, all "Running" processing statuses are changed to "Undone" on the queue table. In this manner, logic consistency is maintained after the power is turned OFF.

As has been described above, in this embodiment, a photographed and obtained X-ray image (a natural image) is reduced, image parameters for this reduced image (reduced natural image) are generated from the default values for the preset image process parameters in accordance with the rules as shown in FIG. 18, image processing using the parameters is performed, and the processed image is screen-displayed on the display 132. In addition, when the operator specifies that image process parameters are changed, image processing is performed for the reduced image using new image process parameters changed in accordance with such specification.

Thus, the apparatus is arranged so as to perform image processing using image process parameters for the reduced image screen-displayed on the display 132, thereby making it possible to perform calculation for image processing at a high speed even in software image processing using a general purpose CPU. As a result, the image processing results can be provided at a high speed.

In addition, when the processing OK button 307 is operated or the region setting button 306 for moving to the next photography is operated, in the case where information such as the natural image at that time, determined image process parameters, and reduction ratio is temporarily stored in the nonvolatile storing unit 128, and an image is selected from the overview display port 304 of the display 132, image process parameters for natural images are generated from the above temporarily stored information in the nonvolatile storing unit 128, and image processing using the parameters is performed.

With such arrangement, the image processing results can be provided at a high speed even in such a case. In this case, image process parameters have already been determined interactively, and thus, image processing can be automatically performed.

Based on the reduction ratio of the reduced natural image, processing for generating image process parameters for the natural image may be performed before storing the image process parameters in the nonvolatile storing unit 128.

Further, an arrangement is made to provide a parameter generating unit 122c1 for reduced natural images which generates image process parameter for images reduction from the predetermined image process parameters (default values); and a parameter generating unit 122c2 for natural images which generates image process parameters for natural images from the last determined image process parameters at the parameter generating unit 122c1 for reduced natural images in accordance with the operator instruction for such determination.

In this manner, image process parameters for the determined reduced natural images are not used for a natural image which is an original of reduction; and therefore, a natural image after image processing can be provided, which is visually similar to the reduced natural image after image processing, screen-displayed on the display 132

Second Embodiment

The second embodiment is a modified example of the above mentioned first embodiment.

That is, in the first embodiment, image processing such as irradiation field recognition, image enhancement, and gradation conversion are performed. In the second embodiment, dynamic range compression is further performed.

Dynamic range compression processing is a process for facilitating check of the contrast of the low density part of an original image. With respect to visual properties of human being, the sensitivity of the contrast at the highlight part is lower than that of the contrast at a middle density part. As dynamic range compression processing, correction is made so as to decrease the pixel value of the highlight part.

Hereinafter, a methodological example of the above dynamic range compression processing will be described.

First, filter processing is performed for the target pixels based on the value of a plurality of pixels, mainly the target pixels, and an input image is smoothened.

Next, the smoothened image is corrected based on a predetermined function, and correction data is created. The predetermined function is a continuous function in which a value for image data having its predetermined threshold value or more (image data which is brighter than a predetermined threshold value) is increased according to the input level.

Then, correction data is subtracted from the input image.

In the case where the above dynamic range compression processing is applied, it is required to change the number of pixels used for smoothing process in processing for natural images and reduced natural images. The number of pixels is changed according to resolution of images targeted for processing.

The present invention is not limited to each of the above mentioned embodiments, and, of course, is variously applicable within the scope not deviating from the gist of the invention.

In addition, in each of the above mentioned embodiments, the image read control unit 122 is arranged so as to change parameters for reduced natural images at the reduced-image adjusting instructing unit 122c according to the user instruction and to create natural image parameters from the final parameters for reduced natural images at the parameter converting unit for natural images 122g. That is, the image read control unit 122 is designed mainly for parameters for reduced natural images without being limited thereto.

Figure 27:
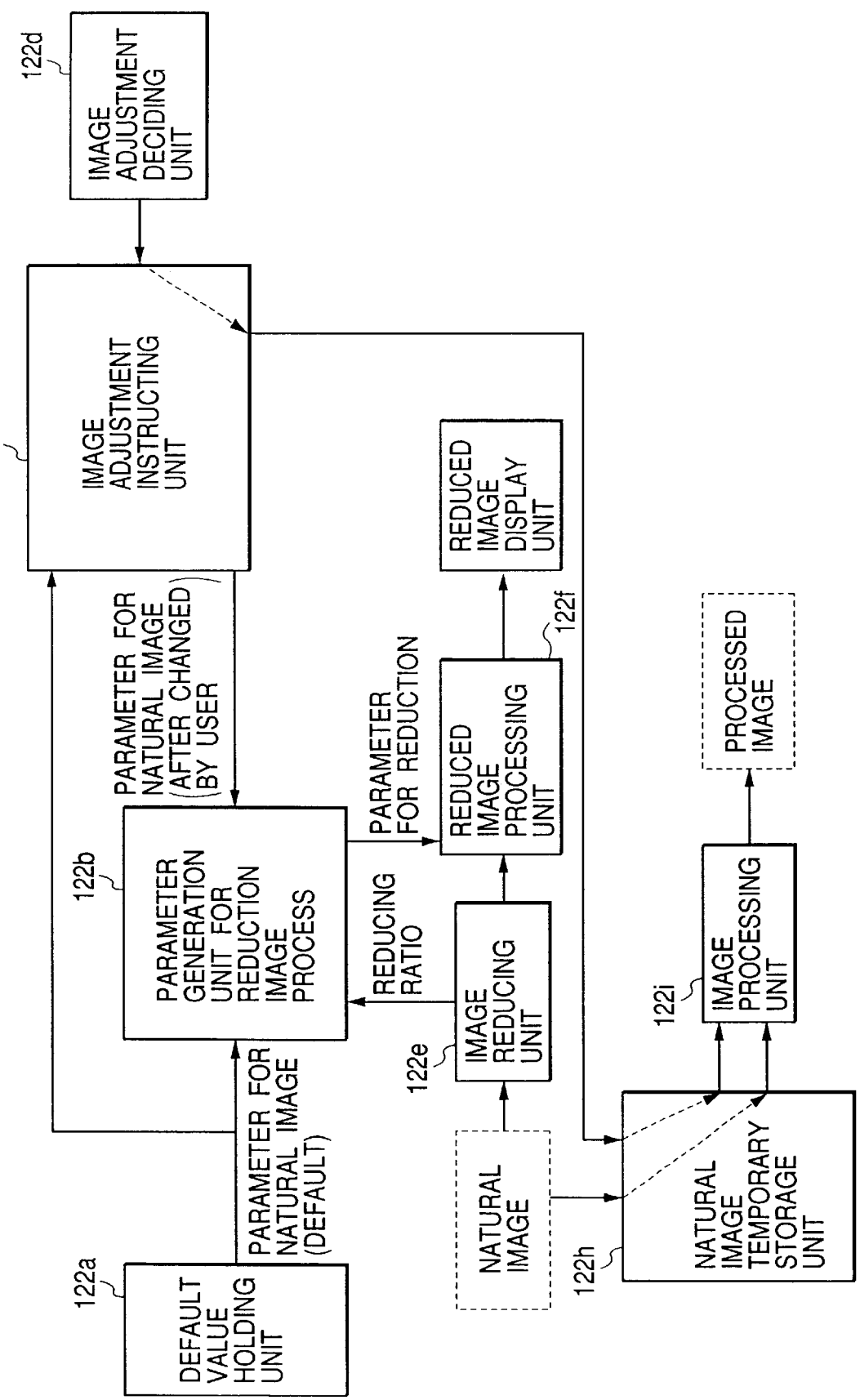
FIG. 27 is a block diagram depicting another configuration example of the above image read control unit.

For example, as shown in FIG. 27, parameters for natural images may be changed at the image adjustment instructing unit 122c according to the user instruction. That is, the image read control unit 122 may be designed mainly for parameters for natural images.

Other Embodiments

An object of the present invention, of course, has been achieved by supplying to a system or apparatus a recording medium storing program codes of software that provides functions of host and terminals according to each of the above mentioned embodiments; and a computer (CPU or MPU) of the system or apparatus reading and executing the stored program codes in the storage medium.

In this case, the program codes itself read from the storage medium achieves the functions according to each of the embodiments, and the storage medium storing these program codes are included in the present invention.

As storage media for supplying program codes, there can be employed ROM, floppy disk, hard disk, optical disk, magneto-optical disk, CD-ROM, CD-R, magnetic tape, non-volatile memory card or the like.

Of course, the present invention is characterized in that the functions of each of the embodiments are achieved by executing the computer read program codes; the OS or the like operating on the computer performs part or all of actual processing based on an instruction of the program codes; and the functions of each of the embodiments are achieved by such processing.

Further, the present invention is characterized in that, after the program codes read out from the storage medium have been written into a memory provided for an inserted extension function board into the computer or a connected function extension unit to the computer, the CPU or the like provided for the function extension board or function extension unit performs part or all of actual processing, and thus the functions of each of the embodiments are achieved by such processing.

As described above, in each of the above mentioned embodiments, the apparatus is arranged so that a first image processing condition used for image processing for reduced images is associated with a second processing condition used for image correction for an original image of the reduced image according to the reduction conditions for the reduced image Specifically, as a display image, a reduced image is generated by reducing an original image, image processing using preset image process parameters (first image processing condition) is performed for the reduced image, and the processed image is displayed on the screen. At this time, when the operator specifies that image process parameters are changed, image processing is performed for the reduced image using the above preset first image process parameters according to such specification.

Thus, the apparatus is arranged so as to perform image processing for the reduced image (display image) using the first image process parameters generated from the preset image process parameters, thereby making it possible to provide image processing results at a high speed in software image processing using a general- purpose CPU.

In addition, when the operator specifies that image process parameters are determined, the original image at this time (original image of a reduced image), the first image parameters, and reduction ratio are stored. From the stored first image process parameters and compression ratio, the second image process parameters (second image processing condition) are generated, and image processing (image correction) is performed for the stored input image using such parameters.

In this case also, image processing results can be provided at a high speed. Further, the first image process parameters has already been determined interactively, and thus, image processing can be automatically performed.

Based on the reduction ratio of the reduced image, processing for generating the second image process parameters may be performed before storing the original image, the first image process parameters, and the reduction ratio.

Further, there are provided means (rules) for generating the first image process parameters from the preset image process parameters; and means (rules) for generating the second image process parameters for the original image from the last determined first image process parameters by the operator instruction. Thus, image process parameters for the determined display image are not employed for the original image which is an original of reduction. The original image after image processing can be provided, which is visually similar to the display image after image processing, displayed on the screen.

Therefore, image processing can be performed at a high speed by a general-purpose CPU. In this manner, the operator can perform image processing job efficiently.

Hence, the present invention is applied to radiation (X-ray) photographing apparatus or system requiring fast image collection, thereby making it possible to provide the apparatus or system inexpensively. In addition, the X-ray technician can perform duties without any burden, thereby making it possible to scan an increased number of patients per hour; and an effect of the invention is economically significant.

The present invention is not limited to the above embodiments and various changes and modifications can be made within the spirit and scope of the present invention. Therefore, to apprize the public of the scope of the present invention the following claims are made.

What is claimed is:

1. An image processing apparatus comprising:

generating means for reducing an original image based on a reduction condition and generating a reduced image;

image processing means for performing image processing for the reduced image based on a set first image processing condition;

display means for displaying the image-processed reduced image;

input means for inputting an instruction for adjusting the first image processing condition;

generating means for generating a second image processing condition for the original image from the adjusted first image processing condition based on the reduction condition; and image processing means for performing image correction for the original image based on the generated second image processing condition.

2. An image processing apparatus according to claim 1, wherein the displaying and adjusting are repeated until a desired reduced image is obtained.

3. An image processing apparatus according to claim 1, further comprising storage means for storing the second image processing condition together with the original image as an image file.

4. An image processing apparatus according to claim 1, wherein the image processing includes irradiation field recognition processing.

5. An image processing apparatus according to claim 1, wherein said image processing means performs a plurality of different image processes, and image processing conditions relating to each image processing operation are associated with each other by a method corresponding to a type of image process.

6. An image processing apparatus according to claim 1, wherein the image processing includes image enhancement processing.

7. An image processing apparatus according to claim 1, wherein the image processing includes gradation conversion processing.

8. An image processing method comprising the steps of:
   reducing an original image based on a reduction condition and generating a reduced image;
   performing image processing for the reduced image based on a set first image processing condition;
   displaying the image-processed reduced image;
   inputting an instruction for adjusting the first image processing condition;
   generating a second image processing condition for the original image from the adjusted first image processing condition based on the reduction condition; and
   performing image processing for the original image based on the generated second image processing condition.

9. A computer-readable storage medium storing code for causing a computer to execute a method comprising the steps of:
   reducing an original image based on a reduction condition and generating a reduced image;
   performing image processing for the reduced image based on a set first image processing condition;
   displaying the image-processed reduced image;
   inputting an instruction for adjusting the first image processing condition;
   generating a second image processing condition for the original image from the adjusted first image processing condition based on the reduction condition; and
   performing image processing for the original image based on the generated a set second image processing condition.

10. An image processing apparatus comprising:
    a generator which reduces an original image based on a reduction condition and generates a reduced image;
    an image processor which performs image processing for the reduced image based on a set first image processing condition;
    a display unit for displaying the image-processed reduced image;
    an input unit for inputting an instruction for adjusting the first image processing condition; and
    an image corrector which performs image correction for the original image based on a set second image processing condition,
    wherein the first and second image processing conditions are image processing conditions for executing the same type of image process, and are associated by the reduction condition.

11. An image processing apparatus according to claim 10, further comprising an image processing condition generator which generates the second image processing condition from the first image processing condition according to the reduction condition.

12. An image processing apparatus according to claim 10, further comprising an image processing condition generator which generates the first image processing condition from the second image processing condition according to the reduction condition.

13. An image processing apparatus according to claim 10, further comprising:
    a display that displays the reduced image; and
    an adjuster which adjusts the first image processing condition according to a user instruction,
    wherein the displaying and adjustment are repeated until a desired reduced image is obtained.

14. An image processing apparatus according to claim 10, further comprising a storage section which stores the second image processing condition together with the original image as an image file.

15. An image processing apparatus according to claim 10, wherein the image processing includes irradiation field recognition processing.

16. An image processing apparatus according to claim 10, wherein said image processor performs a plurality of different image processes, and image processing conditions relating to each image processing operation are associated with each other by a method corresponding to a type of image process.

* * * * *

UNITED STATES PATENT AND TRADEMARK OFFICE
CERTIFICATE OF CORRECTION

PATENT NO.    : 6,671,394 B1
DATED         : December 30, 2003
INVENTOR(S)   : Sako It is certified that error appears in the above-identified patent and that said Letters Patent is hereby corrected as shown below:

Column 3,
Line 2, "at-an" should read -- at an --.

Column 8,
Line 47, "time-" should read -- time --.

Column 11,
Line 5, "area.)" should read -- area), --.

Column 17,
Line 43, "parameter" should be deleted.

Column 21,
Line 47, "statues." should read -- statuses --.

Column 23,
Line 11, ""undone"", should read -- ""Undone"" --.

Column 24,
Line 49, ""undone"", should read -- ""Undone"" --.

Column 25,
Line 20, "operators" should read -- operator --.

Column 26,
Line 18, "display 132" should read -- display 132. --

UNITED STATES PATENT AND TRADEMARK OFFICE
CERTIFICATE OF CORRECTION

PATENT NO. : 6,671,394 B1
DATED : December 30, 2003
INVENTOR(S) : Sako

It is certified that error appears in the above-identified patent and that said Letters Patent is hereby corrected as shown below:

<u>Column 29,</u>
Line 42, "a set" should be deleted.

Signed and Sealed this

Twenty-eighth Day of December, 2004

JON W. DUDAS
*Director of the United States Patent and Trademark Office*